(12) United States Patent
Salama

(10) Patent No.: US 11,241,393 B2
(45) Date of Patent: Feb. 8, 2022

(54) ORGANOSILICON CARRIERS FOR USE IN TREATING INFECTIONS AND/OR DISEASES CAUSED BY SARS VIRUSES

(71) Applicant: Zoser B. Salama, Ravensburg (DE)

(72) Inventor: Zoser B. Salama, Ravensburg (DE)

( * ) Notice: Subject to any disclaimer, the term of this patent is extended or adjusted under 35 U.S.C. 154(b) by 0 days.

(21) Appl. No.: 16/871,317

(22) Filed: May 11, 2020

(65) Prior Publication Data

US 2021/0346305 A1      Nov. 11, 2021

(51) Int. Cl.
*A61K 9/51*      (2006.01)
*A61K 31/7004*      (2006.01)
*A61K 9/127*      (2006.01)

(52) U.S. Cl.
CPC .......... *A61K 9/5123* (2013.01); *A61K 9/1272* (2013.01); *A61K 31/7004* (2013.01)

(58) Field of Classification Search
None
See application file for complete search history.

(56) References Cited

U.S. PATENT DOCUMENTS

2010/0247578 A1\* 9/2010 Salama ................ A61K 9/1272
424/275.1

FOREIGN PATENT DOCUMENTS

| DE | 102005053011 | A1 \* | 5/2007 | ........... A61K 31/695 |
| DE | 102005053011 | A1 | 5/2007 | |
| EP | 0483465 | A1 | 5/1992 | |
| WO | 2007051462 | A2 | 5/2007 | |
| WO | 2011134673 | A1 | 11/2011 | |
| WO | WO-2011134673 | A1 \* | 11/2011 | ........... B60K 17/046 |

OTHER PUBLICATIONS

Google Patents. English Translation of DE 102005053011 A1. Obtained from https://patents.google.com/patent/DE102005053011A1/en?oq=DE+102005053011 on Jan. 7, 2021, originally published in German on May 10, 2007, pp. 1-34. (Year: 2007).\*
Julie Dyall, et al. "Middle East Respiratory Syndrome and Severe Acute Respiratory Syndrome: Current Therapeutic Options and Potential Targets for Novel Therapies." Drugs, vol. 77, 2017, pp. 1935-1966. (Year: 2017).\*
Dwight L. McKee, Ariane Sternberg, Ulrike Stange, Stefan Laufer, Cord Naujokat. "Candidate drugs against SARS-CoV-2 and COVID-19." Pharmacological Research 157 (2020) publication 104859, pp. 1-9, available online Apr. 29, 2020. (Year: 2020).\*
Shuai Xia, Yun Zhu, Meiqin Liu, Qiaoshuai Lan, Wei Xu, Yanling Wu, Tianlei Ying, Shuwen Liu, Zhengli Shi, Shibo Jiang and Lu Lu. "Fusion mechanism of 2019-nCoV and fusion inhibitors targeting HR1 domain in spike protein." Cellular & Molecular Immunology, vol. 17, pp. 765-767, Feb. 11, 2020. (Year: 2020).\*

\* cited by examiner

*Primary Examiner* — Isaac Shomer
(74) *Attorney, Agent, or Firm* — Blue Filament Law PLLC

(57) ABSTRACT

A method for treating, attenuating or inhibiting an infection and/or disease associated with a SARS virus in a subject is provided that includes administering a pharmaceutical composition to the subject. The composition includes an organosilicone carrier with one or more active substances that block and/or inhibit an ACE2 receptor in a host cell of the subject, the spike protein of a SARS virus and/or internal components of a virion of the SARS virus.

12 Claims, 15 Drawing Sheets

1 Encapsulated ACE2-Receptor Inhibitor
2 Siosome
3 ACE 2 Inhibitor
4 ACE 2 Receptor
5 Cell Membrane
6 Host Cell Blocking the ACE 2 Receptors in the host cells using the ACE 2 inhibitor on the surface of the siosomes and the encapsulated ACE 2 inhibitors in the siosomes after release..

Blocking the ACE 2 Receptors in the host cells using the ACE 2 inhibitor on the surface of the siosomes and the encapsulated ACE 2 inhibitors in

Inhibition of the SARS-Co2 V : Blocking the spike (s) structural proteins with the effectors on the outer layer of the siosomes

Structures of silanes/siosomes models with the different functions to provide a novel multi-target and delivery organosilicon siosomes nanosystem
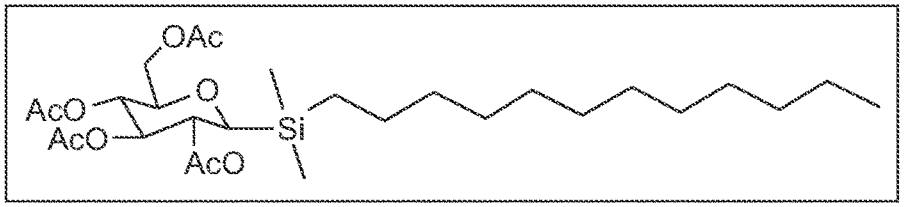
(1) 1-O-Dimethyl(dodecyl)silyl-(2,3,4,6-O-tetraacetyl-b-D-glucopyranosid)
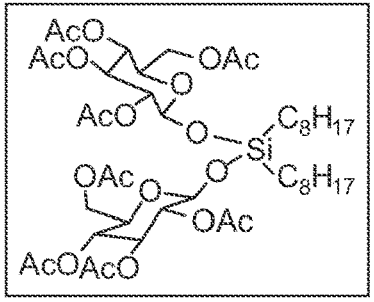
(2) 1-O-Dioctylsilyl-di(2,3,4,6-O-tetraacetyl-b-D-galactopyranosid)
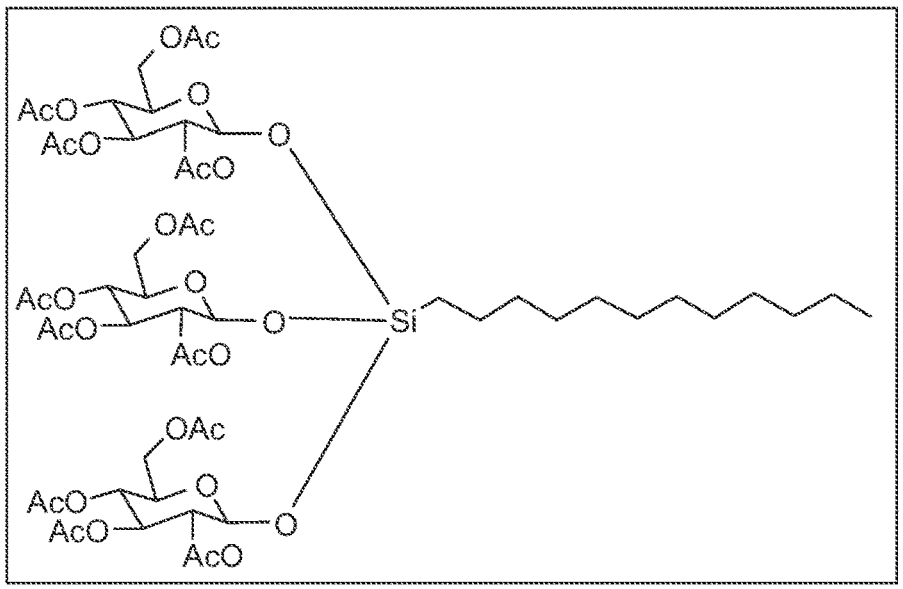
(3) Dodecylsilyl-tris(2,3,4,6-O-tetraacetyl-b-D-glucopyranosid)
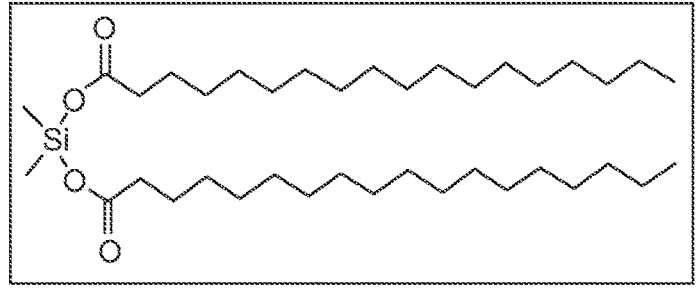
(4) Di(octadecanoyloxy)dimethylsilan
FIG. 5

IMPORTANCE OF SUGAR RESIDUES IN THE ORGANOSILICON COMPOUNTS AND SIOSOMES®

Create the potential for targeted binding against viruses, bacteria and cancer cells.

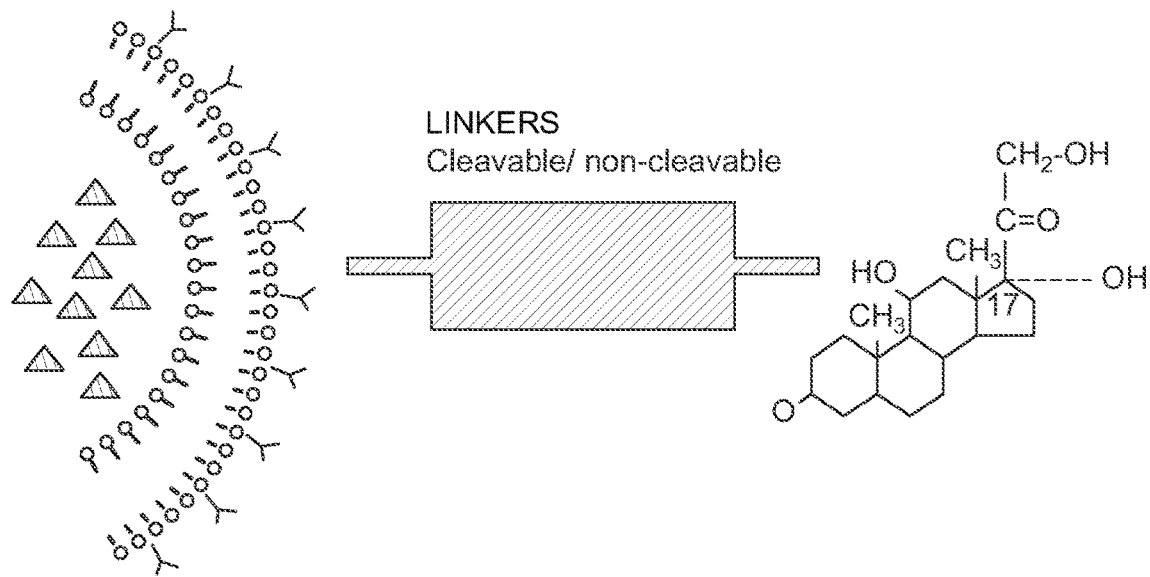
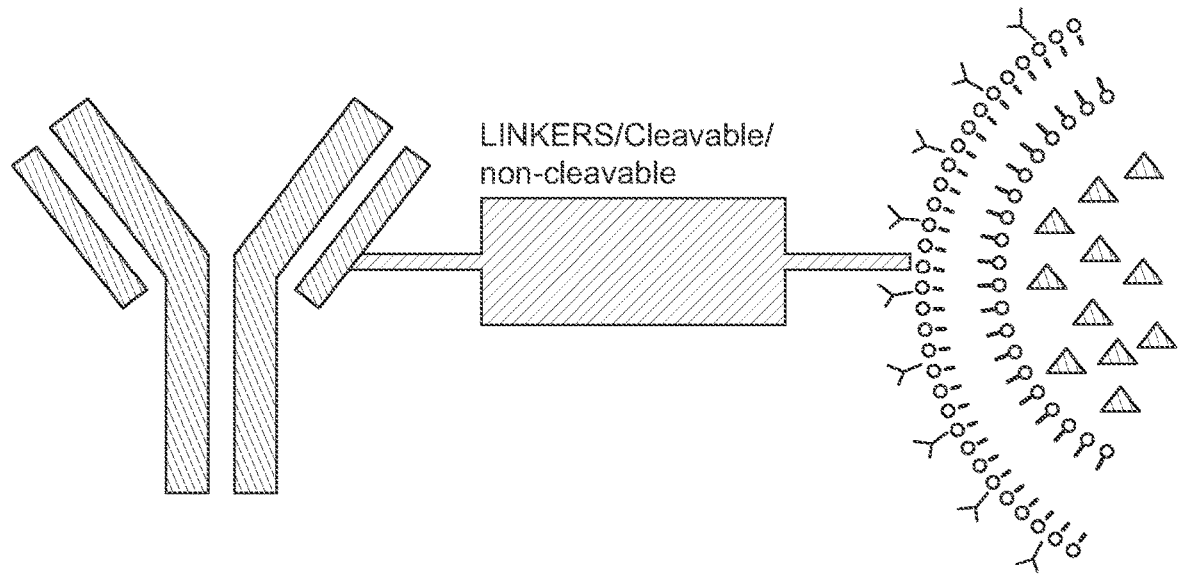
FIG. 12

Siosomes - Genetic Material - Conjugates (SGMC)
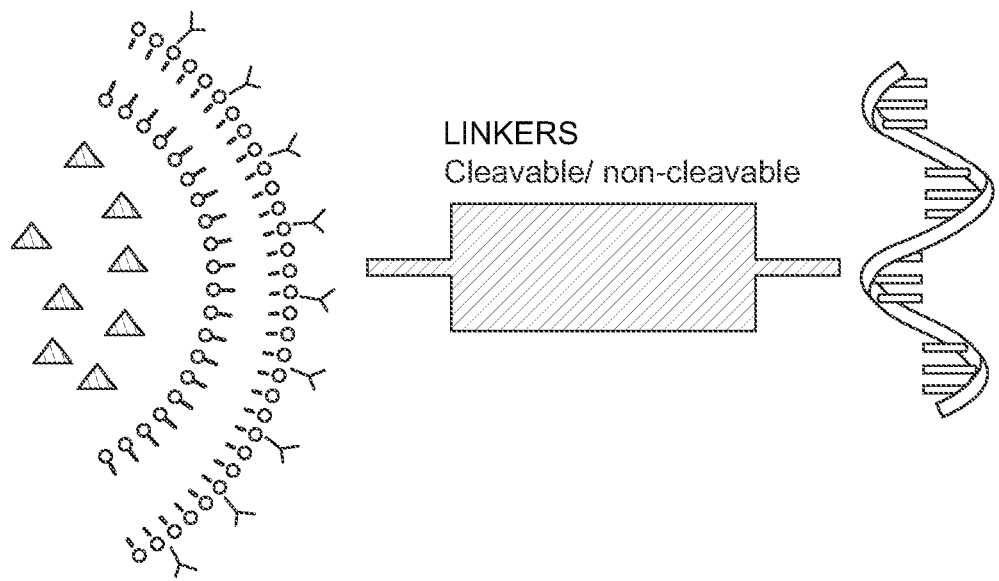
Siosomes - Antiviral Drugs - Conjugates (SADC)
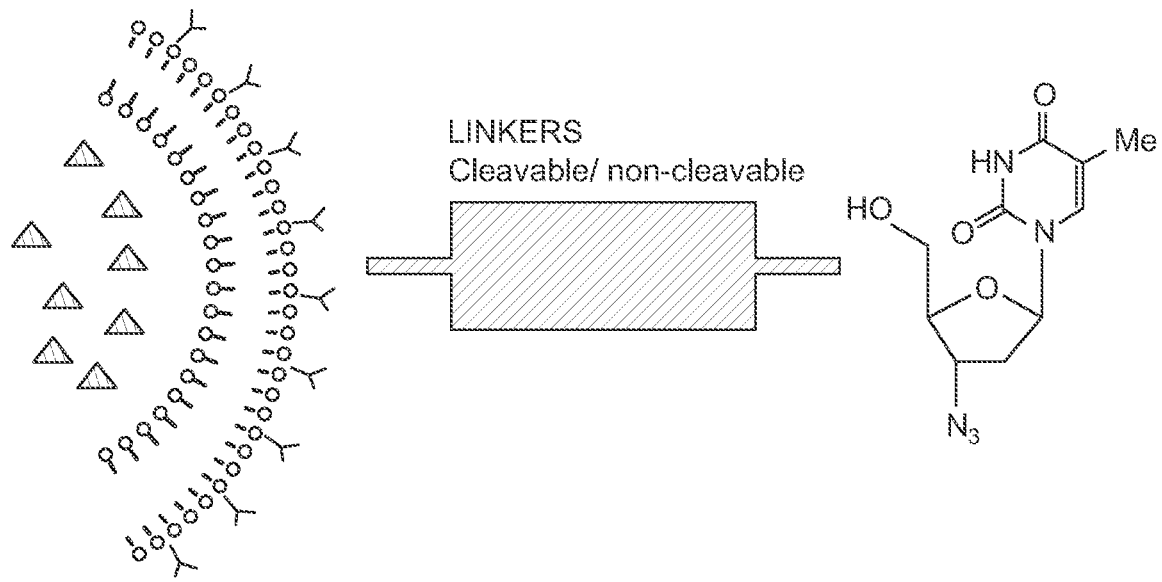
FIG. 13

**PREPARATION OF THE MULTI-TARGET AND DELIVERY SIOSOMES ®
FOR THE PROPHYLAXIS, ATTENUATION AND/ OR TREATMENT OF
THE INFECTIONS CAUSED BY THE SARS CO 2-V**

```
┌─────────────────┐      ┌─────────────────┐      ┌─────────────────┐
│   SIOSOMES 1    │      │   SIOSOMES 2    │      │   SIOSOMES 3    │
├─────────────────┤      ├─────────────────┤      ├─────────────────┤
│ Blocking the    │      │ Blocking agents │      │ Inhibitors for  │
│ ACE2 Receptors  │      │ of the spike    │      │ viral RNA       │
│ Lyophylized     │      │ protein Lyophy- │      │ Lyophylized     │
│ Powder 1        │      │ lized Powder 2  │      │ Powder 3        │
└────────┬────────┘      └────────┬────────┘      └────────┬────────┘
         │                        │                        │
         └────────────────────────┼────────────────────────┘
                                  │
                ┌─────────────────┴──────────────────┐
                │ Combined Lyophylized Powder        │
                │ Composition Compromising Siosomer  │
                │ 1,2,3 at a ratio of X:Y:Z          │
                └─────────────────┬──────────────────┘
         ┌────────────────────────┼────────────────────────┐
┌────────┴────────┐      ┌────────┴────────┐      ┌────────┴────────┐
│   PARENTERAL    │      │      ORAL       │      │     NASAL       │
└─────────────────┘      └─────────────────┘      └─────────────────┘
```

FIG. 15

ORGANOSILICON CARRIERS FOR USE IN TREATING INFECTIONS AND/OR DISEASES CAUSED BY SARS VIRUSES

FIELD OF THE INVENTION

The present invention is directed to organosilicon carriers for use in methods of treating disease associated with a SARS virus. The invention further relates to nanoparticles, compounds, compositions and methods to provide delivery systems comprising organosilicon carriers, preferably multi-target delivery systems, for treating, attenuating and/or preventing viral infections and diseases, in particular those causing severe acute respiratory syndromes (SARS) in human patients or other animal hosts.

In some embodiments, the organosilicon/sugar organosilicon nano particles are encapsulated, entrapped, conjugated or chemically linked, preferably with one or more of the following: Carbohydrates, lipids, amino acids, peptides, proteins, ACE-2 receptor inhibitors, inhibitors of the lung cell receptors, antiviral agents, antibacterial agents, genetic materials (RNA, DNA, mRNA, siRNA), antigens, antibodies, immuno-agents, anti-inflammatory agents, antitumor agents, navigation molecules, GSH, oxidants, metal oxides (iron oxides, sodium meta arsenite, oxoplatin), organosilicon compounds, Remdesivir, corticosteroids, Kaletra and Avigan.

Severe acute respiratory syndrome (SARS) is a new infectious disease caused by a novel coronavirus that leads to deleterious pulmonary pathological features. Due to its high morbidity and mortality and widespread occurrence, SARS has evolved as an important respiratory disease which may be encountered everywhere in the world. The potential mutability of the SARS-CoV 1 genome has led to new SARS-CoV-2 outbreaks and several regions of the viral genomes open reading frames have been identified which may contribute to the severe virulence of the virus. With regard to the pathogenesis of SARS, several mechanisms involving both direct effects on target cells and indirect effects via the immune system may exist.

Vaccination would offer the most attractive approach to prevent new epidemics of SARS, but the development of vaccines is difficult due to missing data on the role of immune system-virus interactions and the potential mutability of the virus.

In 2003, an outbreak of SARS started in China and spread to other countries before ending in 2004. The Virus SARS-CoV-2 that causes COVID-19 is similar to the one that caused the 2003 SARS outbreak. Both are types of the coronaviruses. Much is still unknown, but COVID-19 spreads faster than the 2003 SARS.

Even in a situation of no new infections, SARS remains a major health hazard, as new epidemics may very likely arise. Therefore, the objective of this invention is to provide carrier systems containing the various multi-target and delivery organosilicon Nano compositions that inhibit, prevent and/or attenuate the previous SARS viruses, SARS-Cov-1 and SARS-CoV-2. These compositions are said to be antiviral agents and models for SARS viruses with high probabilities of possible further genome mutations, which may occur in the future according to virologists.

This will be of great benefit to the understanding of the mode of action of the compositions according to the invention and the viral mechanism of the viruses taking the fact into consideration that until today not a single drug is approved for the treatment of any SARS virus. Therefore, the world experiences the loss of hundreds of thousands of human lives and unimaginable economic damage caused by the virus-CoV-2.

Furthermore, the subject matter of this invention is to provide methods for the preparation of the carrier systems containing the various multi-target and delivery organosilicon Nano compositions that inhibit, prevent and/or attenuate the previous SARS viruses, for example SARS-CoV-1 and SARS-CoV-2.

It is also an object of the present invention to provide organosilicon and sugar organosilicon compounds and their derivatives with antiviral properties.

In addition, the objective of the present patent is to provide a method for producing said antiviral organosilicon siosomes by using antiviral silanes and/or sugar silanes without the encapsulation, entrapment and/or conjugation of any compounds and/or reference substances.

Furthermore, the subject matter of this invention is to provide a transfection agent to enhance the penetration of the multi-target and delivery siosomes into the virion, and to interact with the internal compartments of the virus such as the nucleocapsid. Therefore, it is an objective of the present invention to provide organosilicon compounds as cationic organosilicon siosomes with the ability to deliver the multi-target and delivery system with the encapsulated, entrapped and/or conjugated active substances into the virion.

Furthermore, the subject matter of this invention to provide methods for the improvement of the targeting, efficacy, bioavailability and physicochemical properties such as solubility and routes of administration such as oral, nasal, and parenteral application forms of the available mono-targeted antiviral drugs and/or agents such as Remdesivir, Kaletra, and Avigan, using the organosilicon multi-target and delivery systems.

The technical solution underlying the present invention is to provide methods and compositions for a multi-target and delivery systems which will be able to:
Block and/or inhibit the ACE2 receptors in the host cells
Block and/or inhibit the spike protein of the SARS Co2 V virus.
Block, interact, change and/or inhibit the internal compartments of the virion in the SARS Co2 V (e.g. RNA-protein nucleocapsid, membrane protein)
Fusion and inhibition of the SARS
Therefore, it is an objective of the present invention to provide silanes and sugar silanes as Nano organosilicon and sugar organosilicon multi-target and delivery systems with the following objectives:
Silanes/sugar silanes Type 1 Module 1): Blocking/inhibition of receptor ACE2 in the host cells (Example 1.1)
Silanes/sugar silanes Type 2 (Module 2): Blocking/inhibition of the spike protein on the surface of the virion (Example 1.2)
Silanes/sugar silanes Type 3 (Module 3): Blocking, interact, change and/or inhibit the virion (Example 1.3).
Type 1, 2, 3 with the sugar molecules on the surface of the Siosomes will be responsible for the virus recognition and the interaction and fusion with the virus.
It is also an object of the present invention to provide a method for the preparation of the composition of each of the types 1, 2 and 3 which could be used as single composition or a mixture of 2 or more.
It Is also an object of this invention to provide a modular system for the multi-target and delivery systems for the attenuation, prevention and/or treatment of the viral inflammation and diseases caused by the SARS viruses that mainly affect the lungs. This modular system consists of the above mentioned three (3) types/Modules of siosomes.

Type/Module 1: for targeting of the ACE2 receptors in the host cells and could be developed for a broad type of lung receptors (Example 1.1).

Type/Module No. 2: for targeting of the spike proteins on the surface of the SARS virus (Example 1.2).

Type/Module 3: for targeting the RNA-protein nucleocapsid and the internal compartment of the virion (Example 1.3).

For all types/modules, specific sugar molecules will be incorporated on the surface of the siosomes which will be most specific and customized for the virus recognition and communication.

There is great need for antiviral pharmaceutical therapies and compositions that can be used immediately upon the first confirmed cases of the viral infections and prior to the outbreak of the epidemic. So far, the world has always lost a lot of time and thousands of lives until the development and production of the appropriate vaccines. These compositions are based on previous experiences with the SARS and other related vaccines.

BACKGROUND OF THE INVENTION

Features of the SARS-CoV-2

Using SARS-CoV as a model, the coronaviruses have the ability to interact with and modify the host intracellular environment during infection. The studies of the mechanism of action of the viruses are revealing a rich set of novel viral proteins that engage, modify, and/or disrupt host cell signaling and nuclear import machinery for the benefit of virus replication.

Angiotensin converting enzym2 (ACE2) in the cellular receptor for SARS coronavirus (SARS-CoV-2) in the lung, heart, intestinal tract, and kidney that is causing the serious epidemic COVID-19.

The SARS CoV-2 is a positive strand RNA that causes severe respiratory syndromes in human.

The resulting outbreak of the coronavirus disease 2019 has emerged as a severe epidemic, claiming very high number of lives worldwide.

The genome of SARS-CoV-2 shares about 80% identity with that of SARS-CoV and about 96% identical to the bat coronavirus Bat CoV Rat G 13.

In the case of SARS CoV-2, the spike glycoprotein (S protein) on the virion surface mediates receptor recognition and membrane fusion.

The spike glycoprotein (S protein) on the virion surface with its subunits S1 which directly binds to the host receptor ACE2, and while S2 is exposed and is cleaved by host proteases, that is critical for viral infections.

Organosilicon carrier systems

Many carrier systems have, due to various attributes, poor targeting of the pharmaceuticals, biological and genetic materials to the tissues and cells of interest (for example due to chemical structure and stability) In such cases the use of a drug delivery and targeting transport system is beneficial. The encapsulation or entrapment of bioactive or pharmaceutical agents within vesicles can assist in the delivery of these agents to cells and tissues in vivo. Liposomes and siosomes represent two such vesicles commonly used as drug delivery systems. Liposomes are typically phospholipid vesicles capable of encapsulating various biological agents, whereas siosomes are non-phospholipid vesicles created from organosilicon compounds with hydrophilic and hydrophobic ends.

Such delivery molecules can alter the bio-distribution and rate of delivery of an encapsulated pharmaceutical or bioactive agent in a number of ways. For example, drugs encapsulated in liposomes or siosomes are protected from interactions with serum factors which may chemically degrade the drug. A drug targeting system that hides molecules from their environment could also allow these molecules to cross into the intestinal endothelium or the blood brain barrier. Encapsulating a chemical entity in a molecule resembling a biological structure has solved some of these problems. Siosomes and liposomes present such a molecule for drug encapsulation, whereby to the immediate chemical environment the Siosomes will seem to be a biological membrane.

The different generations of Silanes, Sugar Silanes and Siosomes according to the below mentioned patents EP0483465B1 and DE102005053011A1 and WO2011/134673A1 and this invention have achieved the following advantages:

Exciting possibilities based on the silicon and organosilicon chemistry of the Silanes Si R4 (FIG. 2) for the synthesis and characterisation of hundreds of Silanes, sugar Silanes and derivatives with different chemical structures and physico-chemical properties.

Development of Silanes, which their chemical structures will be as biomimetics for the cell membrane (e.g. the most recent generation of the Silanes "sugar Silanes" with fatty acids, sugars, peptides, and nucleosides.

Development of charged Silanes/sugar Silanes as cationic, anionic and zwitterionic, which could be adjusted chemically for the different applications such as the specific cellular and intracellular delivery and targeting of siRNA, anticancer agents such as doxorubicin, pharmaceuticals, biologicals, genetic materials and cosmetic agents.

Development of charged and uncharged Silanes with functional chemical moieties, which will be appropriate for the covalent and/or non-covalent coupling to specific molecules such as antigens, monoclonal antibodies, proteins, small and large molecules.

Investigation of the biological activities of the non-aggregated form of the Silanes such as anticancer, antiviral, antibacterial properties. The objective will be to develop combined therapeutic systems within the Siosome drug delivery and targeting system. In this case the Silanes/sugar Silanes will have its own biological activity. This may have impact on the specific targeting and initial interaction with the cell membrane's ligands and/or receptors.

The main objective according to this invention is to provide biocompatible and specific (customized) multi delivery and targeting systems for pharmaceuticals, biologicals, genetic materials with the following advantages:

Control systemic and intracellular delivery and targeting

Increase the bioavailability and efficacy at the pathological site

Improvement of the solubility of insoluble and sparingly soluble molecules

Reduce the toxicity and side effects

Increase the safety due to specific targeting

Improvement of the patient's quality of life due to the reduction in toxicity

Reduction of the therapy costs (lower dose, less toxicity and side effects)

As a result of the above mention characteristics, it is apparent that Silicon is a far better molecule in terms of easy in Chemistry (reaction with the silicon central atom, formation of linkers (cleavable or non-cleavable) with the active agents when compared with Carbon. The ability to substitute the R molecules at easy allows the combination of a large repertoire other molecules. This will allow many different possibilities and flexibility for the carrier systems according to the invention.

What is surprisingly and unexpected is that the Silane molecules depending on the R groups can demonstrate inherent qualities. These inherent qualities can allow the Silane molecule to act as a drug or an API.

According to the examples of this invention, it is surprisingly that a number of sugar silanes and siosomes have shown antiviral and anticancer activities.

The use of organosilicon molecules in place of phospholipids provides multiple advantages. Organosilicon molecules are more stable at high temperatures, and the vesicles formed from them (siosomes) demonstrate significant advantages in regards to the stability of vesicular entrapments. Liposomes, or other vesicles such as virosomes or niosomes, have the disadvantages of low encapsulation efficiency and poor stability at high temperatures and/or levels of light exposure. Moreover they are not easily reproducible in a defined chemical composition. This results in an unacceptable variability of final product when preparing pharmaceutical agents using liposome particles.

The long chain di(acyloxy)dialkoxy-silanes and tetra(acyloxy)silanes, a method to prepare them, a method using them to prepare vesicles, and siosome vesicles consisting of the long-chain di(acyloxy)dialkylsilanes and their use have been described in the following patents: EP 0483465 B1 "Long chain di(alkoxy)dialkysilanes, di(alkoxy)diarysilanes, and tetra(alkoxy)silanes, methods to prepare them, vesicles prepared from them (Siosomes) and their use as vesicles for active substances", DE 102005053011 A1 "Tetra organic silicone compounds, their use, their use for preparation of vesicles, vesicles prepared from them (Siosomes) and using them as active agents, as vesicles for active agents and for the preparation of vesicles", and PCT/DE2006/001948 "Use of Tetraorganosilicon compounds".

WO 2011/134675 A1 "Carrier and targeting system comprising a siosomal composition for intracellular delivery and targeting of active substances" has described these carrier systems comprising a composition of active substances, organosilicon, Peptide organosilicon, amino acids, organosilicon, lipids and/or their derivatives. These carrier and targeting systems are obtainable by the different procedures according to the patent as lyophilised powder. The patent has described further the methods for preparing and administering the carrier and targeting system as well as transfecting a cell with the different agents.

Despite success as drug delivery systems, the traditional liposome and siosome entrapments and encapsulations as disclosed in the prior art are limited in regards to the efficiency of the cellular and intracellular targeting of the human tissues, cells and receptors and viruses using specific molecules on the surface (outer layer) of the siosomes such as: amino acids, peptides, proteins, ACE-2 receptor inhibitors, Inhibitors of the Lung Cell, receptors, antiviral agents, antibacterial agents, genetic materials (RNA, DNA, mRNA, siRNA), antigens, antibodies, immuno-agents, anti-inflammatory agents, antitumor agents, antivirus agents, navigation molecules, GSH, Oxidants, metal oxides (iron oxides, sodium meta-arsenide, oxoplatin).

These vesicles are also usually limited to the encapsulation of only one active agent. This limitation has disadvantages in the use of vesicles as carriers for more than one agent and/or preparation of vaccines, because it is difficult to encapsulate a mixture of biologically active substances.

According to the relevant prior art (WO 2011/134673 A1"), an example of the preparation process of the carrier systems:

a) mixing one or more organosilicon compounds, selected from the group comprising: Organosilicon, sugar organosilicon, amino sugar organosilicon compounds, their derivatives, salts and/or the vesicles formed from them, with one or more biological agents, selected from the group comprising: antigens, pre-antigens, antigen conjugates, antibodies, antibody conjugates, allergens, allergen extracts, nucleic acids, plasmids, proteins, peptides, pharmaceutical agents, immunologically active substances and/or cosmetics, in solution at a pH value between 7 and 8, preferably 7.4, followed by b) Homogenization or sonication of the mixture, followed by c) Sterile filtration of the mixture, followed by Lyophilisation.

There has been no organosilicon carrier system described in the prior art, capable of obtaining the multi-targeting molecule(s) on the surface (outer layer) of the siosomes nanoparticles. These molecules as targeting (navigating molecule(s)) are not limited to carbohydrate, lipid amino acids, peptides, proteins, ACE-2 receptor inhibitors, Inhibitors of the Lung Cell, receptors, antiviral agents, antibacterial agents, genetic materials (RNA, DNA, mRNA, siRNA), antigens, antibodies, immuno-agents, anti-inflammatory agents, antitumor agents, antivirus agents, navigation molecules, GSH, Oxidants, metal oxides (iron oxides, sodium meta-arsenide, oxoplatin), Remdesivir, corticosteroids, Kaletra, Avigan, and positive strand RNA virus.

This is particularly relevant in the preparation and administration of the organosilicon multi-target and delivery siosomes nanoparticles. Human tissues, cells and receptors recognize particular parts of the organosilicon carriers with the different navigators and molecules. Importantly, it is the three dimensional structure of the target which is recognized by the specific targeting molecule(s) on the surface of the siosomes According to the invention and the examples of the invention the application of organosilicon carriers with the encapsulated, entrapped and/or conjugated molecules also surprisingly and unexpected benefits from the controlled release and distribution provided by the use of organosilicon molecules.

SUMMARY OF THE INVENTION

The technical problem underlying the present invention is to provide a organosilicon carrier system, and corresponding nanosystems, compounds, compositions, and methods with the objectives:

1. Delivery and multi-cellular and intracellular targeting of ACE-2 Receptor in the lung epithelial cells and others.
2. Delivery and multi-targeting of the spike glycoprotein (S protein) on the virion surface with its subunits S1 and S2 of the SARS-CoV-2 Virus as a model for SARS viruses, which are responsible for the surface mediate receptor recognition and membrane fusion "The objective according to the invention is Blocking the spike glycoprotein (S protein) on the virion surface with its subunits S1 and S2 of the SARS-CoV-2 Virus"
3. Delivery and multi-targeting of the Internal helical RNA-protein nucleocapsid inside the virion of the SARS-CoV-2 using the organosilicon siosomes nanoparticle and in addition blocking the late stages of virus assembly and/or damage the virus replication strategy This will cause the "Inhibition of the SARS-CoV-2 virus".
4. Treatment, prevention and/or attenuation of the viral infections, in particularly which are causing severe acute respiratory syndrome SARS in human or other animal hosts known as COVID-19 disease. Caused by SARS Co 2 V virus.

The problem is solved by the features of the independent claims. Preferred embodiments of the present invention are provided by the dependent claims.

The object of the invention is therefore to provide a carrier and preferably a targeting system for the intracellular delivery and release of one or more siosome encapsulated, entrapped, conjugated and/or linked (cleavable or un-cleavable) active substances, comprising a composition of active substance, with one or more of organosilicon, sugar organosilicon and/or amino-sugar organosilicon.

The invention therefore relates to a method for treating, attenuating or inhibiting an infection and/or disease associated with a SARS virus in a subject, comprising administering a pharmaceutical composition to the subject, wherein the composition comprises an organosilicon carrier with one or more active substances that block and/or inhibit an ACE2 receptor in a host cell of the subject, the spike protein of a SARS virus and/or internal components of a virion of the SARS virus.

In one embodiment, the SARS virus is a SARS CoV-2.

In one embodiment, the organosilicon carrier is an "organosilicon multi-target and delivery carrier" or a "organosilicon delivery carrier". This language may be used, in some embodiments, in place of "organosilicone carrier". This "organosilicon multi-target and delivery carrier" or "organosilicon delivery carrier" defines an organosilicon carrier with delivery function, preferably to multiple targets, i.e. such a carrier enhances delivery of one or more active substances, that is incorporated, entrapped, complexed or otherwise associated with the organosilicon carrier, to a target cell, tissue, organ, or other desired location of the subject.

In one embodiment, organosilicon carrier is a targeting system for the intracellular delivery and release of one or more siosome encapsulated, entrapped, conjugated and/or linked (cleavable or un-cleavable) active substances.

In one embodiment, the organosilicon carrier comprises an organosilicon, sugar organosilicon, or amino-sugar organosilicon compound according to the general formula (I):

General Formula (I)

$$\begin{array}{c} R1 \\ \diagdown \\ R2 \end{array} Si \begin{array}{c} R3 \\ \diagup \\ R4 \end{array}$$

whereby R1, R2, R3, can be the same or different,
whereby R1, R2, R3=Mono, Di-, oligosaccharide, amino sugar, carbohydrate, nucleotide,
whereby R4=Fatty acid.

In one embodiment, the chemical groups and/or residues of R1, R2, R3 and R4 of the general formula (I), which can be the same or different, are selected from the group of substances consisting of: Carbohydrates, lipids, amino acids, peptides, proteins, ACE-2 receptor inhibitors, nucleosides, inhibitors of the lung cell receptors, antiviral agents, antibacterial Agents, genetic materials (RNA, DNA, mRNA, siRNA), antigens, antibodies, immuno-agents, anti-inflammatory agents, antitumor agents, cardio-protectors, hepato-protectors, navigation molecules, GSH, oxidants, metal oxides (iron oxides, sodium meta arsenite, oxoplatin), organosilicon compounds, Remdesivir, corticosteroids, Kaletra and Avigan.

In one embodiment, the chemical groups and/or residues of R1, R2, R3 and R4 of the general formula (I), which can be the same or different, are conjugated by cleavable or non-cleavable linkers with one or more of the substances selected from the group consisting of: Monoclonal antibodies, carbohydrate, lipids, amino acids, peptides, proteins, ACE-2 receptor inhibitors, nucleoside, inhibitors of the lung cell receptors, antiviral agents, antibacterial agents, genetic materials (RNA, DNA, mRNA, siRNA), antigens, antibodies, immuno-agents, anti-inflammatory agents, antitumor agents, cardio-protectors, hepato-protectors navigation molecules, GSH, oxidants, metal oxides (iron oxides, sodium meta arsenite, oxoplatin), organosilicon compounds, Remdesivir, corticosteroids, Kaletra and Avigan.

In one embodiment, one or more cationic lipids are covalently attached to the organosilicon and/or as a derivative of the chemical groups and/or residues of R1, R2, R3 and R4 of the or $$-OOC-R-\overset{CH_3}{\underset{CH_3}{\overset{+}{N}}}-CH_3$$

or $$-OOC-R-\overset{CH_3}{\underset{CH_3}{\overset{+}{N}}}-CH_3$$

or $$\begin{array}{c} -Oleoyl-O \\ \diagdown \\ -Oleoyl-O \end{array} C-CH_2-\overset{CH_3}{\underset{CH_3}{\overset{+}{N}}}-CH_3$$

In one embodiment, the organosilicon carrier is in the form of a siosome that is configured as a transfection agent to transfect the virus.

In one embodiment, the composition is a formulation comprising siosome nanoparticles.

In one embodiment, the one or more active substances, selected from the group consisting of monoclonal antibodies carbohydrate, lipids, amino acids, peptides, proteins, ACE-2 receptor inhibitors, nucleoside, inhibitors of the lung cell receptors, antiviral agents, antibacterial Agents, genetic materials (RNA, DNA, mRNA, siRNA), antigens, antibodies, immuno-agents, anti-inflammatory agents, antitumor agents, cardio-protectors, hepato-protectors navigation molecules, GSH, oxidants, metal oxides (iron oxides, sodium meta arsenite, oxoplatin), organosilicon compounds, Remdesivir, corticosteroids, Kaletra and Avigan, are encapsulated, entrapped and/or conjugated in siosome nanoparticles.

In one embodiment, the organosilicon carrier comprises modular groups according to their function, wherein the modular groups are:

Module 1 to block and/or inhibit the ACE2 receptors in the host cells;

Module 2 to block and/or inhibit the spike protein of the SARS Co2 V virus; and

Module 3 to block, interact, change and/or inhibit the internal compartments of the virion in SARS Co2 V (e.g. RNA-protein nucleocapsid, membrane proteins).

In one embodiment, the modules comprise the compositions:

Module 1: Siosomes with specific ACE2 receptor inhibitors and/or carbohydrates on the surface of the siosomes and/or specific ACE2 inhibitors encapsulated, entrapped and/or conjugated in the siosomes;

Module 2: Siosomes with specific inhibitors of the spike protein and carbohydrate molecules on the surface of the siosomes; and Module 3.1: Siosomes encapsulated, entrapped and/or conjugated to polymerase inhibitors and siosomes transfection agents and/or Module 3.2: Siosomes with polymerase inhibitors on the surface of the siosomes connected via cleavable and/or non-cleavable linkers.

In one embodiment, the organosilicon carrier is obtained by:

a. mixing one or more organosilicon, sugar organosilicon, amino-sugar organosilicon in a solvent and/or the vesicles formed from them, with one or more of the active substances at selected pH, salt concentration and temperature;

b. homogenization, sonication and/or extrusion of the mixture, followed by c. separation of the free active substance, d. sterile filtration of the mixture, e. lypholization, and f. reconstitution to form a siosome of the multi-target and delivery system.

In one embodiment, the composition is administered in combination with additional antiviral therapies in patients with symptoms of a SARS infection.

In one embodiment, the treatment comprises administration of a pharmaceutically effective dose of a second agent.

In one embodiment, the second agent is selected from the group consisting of amino acids (such as arginine), carnitine/carnitine derivatives, neurotransmitters such as dopamine, vitamins, caffeine, antifibrotic agents, memory activating agents, neuroprotective agents, cardio-protective agents, antidiabetic agents, drugs for the prophylaxis and/or treatment of thrombosis, glutamate-antagonist, glutathione GSH, anti-Alzheimer's disease agents, antioxidants, anti-AIDS drugs, NSAIDS, antipsychotic drugs such as buspirone, antidepressants such as selective serotinin reuptake inhibitors (SSRIs), mood stabilizers, anticonvulsant, antigens, antibodies, genetic materials such as siRNA, RNA, DNA, catecholamine's, hormones and sympatholytic (adrenergic blocking) agents such as ergot alkaloids.

In one embodiment, the following silanes and sugar silanes, that have antiviral activities against the enveloped viruses Human Cytomegalvirus (HCMV), Influenza Virus A (H3N2) and/or Vaccina Virus, are employed:

2-(Dimethyldecylsilyl)ethyl-b-D-glucopyranoside,
2-(Dimethyldodecylsilyl)ethyl-b-D-glucopyranoside,
Butyldimethylsilyl-a-D-galactopyranoside,
Dodecyldimethylsilyl-a-D-glucopyranoside,
1-O-Dioctadecylsilyl-di(2,3,4,6-O-tetraacetyl-b-D-galactopyranoside),
1-O-Dimethyl(dodecyl)silyl-(2,3,4,6-O-tetraacetyl-b-D-glucopyranoside),
1-O-Dimethyl(octadecyl)silyl-(2,3,4,6-O-tetraacetyl-b-D-glucopyranoside),
Di(dodecanoyloxy)diphenylsilane,
Di(hexadecanoyloxy)diphenylsilane, or
Di(undecanoyloxy)dimethylsilane.

In one embodiment, the organosilicon carrier comprises neurotransmitters and/or amino acids as navigators incorporated on the surface of the siosomes, and/or encapsulated, entrapped and/or conjugated in the siosomes, configured for the targeting of the brain and/or central nervous system.

In one embodiment, the organosilicon carrier comprises gastro intestinal tract (GIT) specific compounds, such as N-acetyl cysteine, glutamine, fumarate, glycolic Acid, sodium glycol cholate, sodium deoxy cholate, sodium caporate, lectins, chitosan and Poly lactic acid, as navigators incorporated on the surface of the siosomes, and/or encapsulated, entrapped and/or conjugated in the siosomes, for the targeting of the gastro intestinal tract and/or colon.

In one embodiment, the composition is administered as one or more modules, each separately or as a mixture, at a single or multiple dose.

In one embodiment, the carrier system is administered via oral, rectal, vaginal, topical, nasal, intradermal, or parenteral administration, or as a transbuccal, sublingual, transmucosal or a sustained release formulation, wherein the parenteral administration is preferably selected from the group consisting of subcutaneous, intravenous, intramuscular and infusion. In a preferred embodiment, the carrier and multi-targeting system of the present invention is characterized in that the organosilicon sugar organosilicon, or amino-sugar organosilicon compounds are characterized by the general formula (1):

$$\begin{array}{c} \text{General Formula 1} \\ R1 \diagdown \diagup R3 \\ Si \\ R2 \diagup \diagdown R4 \end{array}$$

Whereby the residues R1, R2, R3 and R4, and the compounds and molecules which are encapsulated, entrapped, conjugated and/or with linkers compounds can be (but not limited) to the following: Carbohydrate, lipid, amino acids, peptides, proteins, ACE-2 receptor inhibitors, Inhibitors of the Lung Cell receptors, antibacterial agents, genetic materials (RNA, DNA, mRNA, siRNA), antigens, antibodies, immuno-agents, anti-inflammatory agents, antitumor agents, antivirus agents, navigation molecules, GSH, Oxidants, metal oxides (iron oxides, sodium meta-arsenite, oxoplatin), Remdesivir®, corticosteroids, Kaletra®, Avigan®, positive strand RNA virus, and sodium meta-arsenite.

In a preferred embody the carrier and multi-targeting system of the present invention is characterized in that the Structures of Silanes/Siosomes models with the different functions to provide a novel multi-target and delivery organosilicon siosomes nano system will be for:

1. Blocking the ACE2 Receptors e.g. in the human lung epithelial cells, heart cell, Kidney, GI and liver using the siosomes nano carrier system (FIG. 1)
2. Blocking the spike glycoprotein (S protein) on the virion surface with its subunits S1 and S2 of the SARS-CoV-2 Virus using the siosomes nanocarrier system (FIG. 2)
3.1 Inhibition of the SARS-CoV-2 virus (Inhibition of viral RNA dependent RNA polymerase, blocking late stage of virus assembly) using in siosomes encapsulated polymerase inhibitors using the siosomes nanocarrier system. (FIG. 3)
3.2 "Inhibition of the SARS-CoV-2 virus (Inhibition of viral RNA dependent RNA polymerase, blocking late stage of virus assembly) using polymerase inhibitors on the surface (outer layer) of the siosomes connected via cleavable and/or noncleavable LINKERS (FIG. 3)

Furthermore In a preferred embody the carrier and multi-targeting system of the present invention is characterized in that the organosilicon sugar organosilicon, or amino-sugar organosilicon compounds and the multi-target and delivery siosomes nano carrier systems prepared thereof are characterized by the general formula (1) could be prepared according the methods to this invention in one or more pharmaceutical formulation (intravenous, oral, nasal. Inhalation) as a composition of the different nano carrier systems with the objectives:

Blocking the spike glycoprotein (S protein) on the virion surface with its subunits S1 and S2 of the SARS-CoV-2 Virus"(FIG. 2).

Inhibition of the SARS-CoV-2 virus"/multi-targeting of the Internal helical RNA-protein nucleocapsid inside the virion (blocking late stage of virus assembly) of the SARS-CoV-2, and/or the dysfunction of the Golgi Apparatus and the transport of the replicated virus from the Golgi Apparatus to the membrane. (FIG. 3)

Blocking the ACE2 Receptors in the human lung epithelial cells using the siosomes nanocarrier system (FIG. 1)

Therefore an object of the invention is to provide a carrier system capable of incorporating the organosilicon molecules according to the General Formula (1) to penetrate (transfect) the virus and to inhibit its function. According to the invention the following compounds will enhance the penetration of the multi-target carrier systems into the virus:

Cationic lipids, glycolipids, phospholipids, cholesterol or derivatives thereof, and equivalent molecules known to those of skill in the art, can also be included in the carrier systems of the present invention. Cationic lipids can comprise preferably DOTMA (N-[1-(2,3-dioleyoxy)propyl]-N, N,N-trimethylammonium-chloride), DODAC (N,N-dioleyl-N,N-dimethylammoniumchloride), DDAB (didodecyldimethylammonium bromide) and stearylamine and other aliphatic amines and the like. Carrier systems containing different types of polar (positively or negatively charged) and neutral (electrochemically neutral) lipids represent another preferred embodiment of the invention, examples of such lipids including phosphatidyl ethanolamine, phosphatidyl Inositol, phosphatidyl glycine, phosphatidyl glycerol, lipofectamine, cholesterol.

DETAILED DESCRIPTION OF THE INVENTION

Features of the Organosilicon Multi-Target and Delivering System

The present invention is directed to provide an organosilicon multiple targeting and delivery system which will be capable of accumulating at target organ, tissue cells or viruses via active and specific targeting agents (for example by incorporating an antibody, saccharide, ACE2 receptor inhibitor, nucleoside, genetic materials, antiviral drugs, peptide, hormones, ligands on the surface of the siosomal nanovesicles Following accumulation at the target site, the siosomal carrier would become capable of fusing/blocking without the need of any external stimulus, and would subsequently interact and/or release any encapsulated or associated drug or active substance in the vicinity of the target cell, or fuse with the target cell, plasma membrane, introducing the drug or active substance into the cell and/or virus cytoplasma. In certain instances, fusion of the carrier with the plasma membrane would be preferred because this would provide more specific drug delivery and hence minimize any adverse effects on normal healthy cells or tissues.

In addition, according to the invention in the case of active substances such as carbohydrate, lipids, amino acids, peptides, proteins, ACE-2 receptor inhibitors, inhibitors of the Lung Cell receptors, antiviral agents, antibacterial Agents, genetic materials (RNA, DNA, mRNA, siRNA), antigens, antibodies, immuno-agents, anti-inflammatory agents, antitumor agents, antivirus agents, navigation molecules, GSH, Oxidants, metal oxides (iron oxides, sodium meta-arsenide, oxoplatin), Remdesivir, corticosteroids, Kaletra, Avigan, and positive strand RNA virus which are generally not permeable to the virus membrane.

Such a fusogenic carrier as the organosilicon siosomes carrier would provide a mechanism whereby the active substance could be delivered at high concentration to its required intracellular site of action e.g. inside the virion of the SARS Co-V-2 virus (FIG. 3). In this case the active substance would not be exposed to acidic conditions and/or degradative enzymes that could be destructive to the said active substances.

In addition the use of the multi-target and delivery system according to the invention have the following advantages:

Improve drug solubility for sparingly soluble active substances;

Control delivery of small molecules, peptides, proteins and nucleic acids and the other active substances;

Increase drug bioavailability at the target and disease site;

Quite surprisingly, the present invention addresses this need by providing such a method.

One aspect of the present invention is the triggered release of the encapsulated or bound active substances upon entry to a virion of the virus. The intra-virion delivery can be released in triggered manner. The multi-target carrier system. once administered the following interactions with the virus will take place:

The sugar molecules on the surface (outer layer) of the siosomes will block the spice protein on the surface of the virus which is responsible for targeting the ACE2 receptor in the host cell in the lung and other tissues such as heart, kidney and gastro-intestinal tract.

The nanoparticles of the siosomes carrier system will fuse with the virus particles through the interactions between their sugar molecules and lipid membranes and therefore inhibit the virus.

The siosomes as the fusogenic carrier system will be taken up by the virus either endocytosis, phagocytosis or pinocytosis. This may occur via sugar interactions with the virion surface to enter the virus via receptor mediated endocytosis. In this form of endocytosis the cytoplasm membrane folds inward to form coated pits (endosome). These vesicles are subsequently carried into the virus cytosol and are fused with the internal virus compartments.

The following interactions could occur inside the virion:
Subsequent interaction between the active substance e.g. antiviral agents on the surface of the siosomes with the nucleocapsid and/or Golgi apparat or other compartments inside the virion.
Interaction of the encapsulated and entrapped active substances upon their release from the siosomes with the nucleocapsid and/or Golgi apparat and other compartment inside the virion.

These interactions will cause the inhibition of the SARS-CoV-2 virus" via the multi-targeting of the nucleocapsid as the Internal helical RNA-protein inside the virion blocking late stage of virus assembly of the SARS-CoV-2, and/or the dysfunction of the Golgi Apparatus and the transport of the replicated virus from the Golgi Apparatus to the membrane in the host cell.

Chemical Structures and Preparation

According to the invention, the following are furthermore preferred embodiments and advantages concerning the multi-targeting of the carrier system:
The chemical structures of multi-targeting and delivery system will allow the specific targeted effect for several recipes at the same time.
Provide many possibilities to chemically incorporate molecules of active substances on the surface of the siosomes, for example but not limited to antiviral drugs such as Remdisivir, Kaletra, Avigan, chlorquine, hydroxychloroquin, genetic materials, protease inhibitors, polymerase inhibitors, peptide, proteins, amino acids, corticosteroids, antibacterial agents, receptor blocker/inhibitors, anticancer agents, navigating and modulating molecules that are specific for cells of interest.
Higher concentration of the active substances at the site of the action due to the available active substances on the surface and enclosed in the siosomes.
Higher specific targeting properties due to the navigation and modifying molecules placed on the surface.

Furthermore, it is a preferred embodiment of the present invention that the method of preparation of the carrier system takes place by:
Selection of the optimal silane/sugar silane.
Chemical synthesis/incorporation of the active substance in the chemical residues R1, R2, R3, and R4 of the silane/sugar silane as described in (FIG. 14).
Preparation, optimization and characterization of the siosomes as the qualified multi-target and delivery system.
The optimization of the multi-target and delivery system will depends on the physicochemical properties of the active substance, its release profile, and the targeted organ, tissue and/or cells of interest.
The silanes/sugar silanes according to the present invention provides enormous possibilities with different molecular structures, size, shape, and charge.

Formulations of the Siosomes as Finished Multi-Target and Delivery Systems for Administration to the Patients.

According to the invention the siosomes could be prepared as long-term stable lyophilized powder which is appropriate for the preparation of any pharmaceutically acceptable formulations such as for intravenous, parenteral intranasal, transdermal, rectal, intravaginal, topical, oral transmucosal carriers, buccal delivery compositions, sublingual formulations, Orodispersible Tablets (ODT), Orodispersible Films (ODF), Orodispersible Granules (Micro-Pellets), Fast Oral Transmucosal (FOT), capsules, tablets, an aqueous suspensions and solutions. or oily suspensions, dispersible powders or granules, emulsions, hard or soft capsules, nano-carriers, liposomes, siosomes, gels, mucosal adhesives, or syrups or elixirs.

The Siosomes prepared from the silanes/sugar silanes using the procedures according to the present invention will offer very specific multi-targeting and delivery nanosystems for tissues, cells and viruses based on the selection of the sugar molecules, and navigating molecules and the active substances on the surface of the siosomes and as encapsulated, entrapped and/or conjugated molecules.

It is known that the sugar molecules such as the glucose, fructose, mannose and others are responsible for the cell recognition and communication.

In addition, the objective of the multi-target and delivery system according to the present invention is to release the active substances from the siosomal nanoparticles to trigger and to enhance the cell or the virus penetration and to target them via the agent and/or biological agent which are encapsulated and entrapped in the siosomes.

The use of the siosomes have shown unexpected the ability to increase the concentration of the encapsulated drug in certain organs, tissues and cells in the body such as in the lung, heart and kidney in comparison to the administered free drug (Table 14).

For example the SARS CoV-2 virus have shown high activity in these organs and could cause tissue damage and organ dysfunction. Therefore it is an objective of the present invention to provide carrier system to target the virus in these organs specifically with encapsulated and entrapped antiviral agent and other active agents.

According to the procedures of the invention, it has been shown that the encapsulated and/or entrapped active substances of the chemostatic and toxic agents including a number of the antiviral agents will not be biologically active in the targeted tissues or viruses until their release from the siosomes. This will have a number of advantages such as:
Improvement of the bioavailability in the target.
Increase the efficacy e.g the antiviral activity.
Increase the safety of the active substance such as antiviral agents
Decrease of the treatment costs Furthermore the subject matter of this invention is to provide a carrier for multi-targeting of viruses and particularly the SARS viruses.

Therefore it is an objective of the SIO-multi-target and delivery systems to provide combined immediate and sustained (retard) release formulation of the encapsulated and/or entrapped siosomes for the prevention, attenuation, treatment of viral infections. The advantages of the combined release formulations according to the invention could be summarized as follows:

The composition according to the SIO-combined release formulations procedures and according to the present invention could consist of a well-defined free and encapsulated and/or entrapped antiviral agents. The total of the antiviral drug content will represent the "Therapeutic Dose" of the Siosomes® formulation. This therapeutic dose could be lower than the therapeutic dose of the standard parenteral anti-viral infusion formulation, due to lower protein binding and different PK/PD profiles (PK=Pharmacokinetics, PD=Pharmacodynamics. These two terms simply mean the relation between the dose, blood level achieved with the drug and the size of the clinical effect).

For example the bioavailability and pharmacokinetic/tissue distribution of the Siosomes®-Complex with the active agent (antiviral drug) will be a combination of the two formulations with different release and efficacy profiles. Only a small part of the combination (free antiviral drug) will have a similar profile as for example, the standard parenteral antiviral infusion formulation. This will result in lower plasma and tissue levels than the standard parenteral antiviral drug and decreased systemic and tissue toxicity. It is known, that the toxicity is dependent on the systemic drug concentration/systemic and tissue/organ drug clearance, bioaccumulation in organs such as liver, spleen, kidney, and lung tissues.

According to the present invention. The Siosomes®-Antivirus-Complex formulations will have a number of further advantages in comparison to the commercially available standard antiviral infusion formulations with free (un-encapsulated drug), e.g. lowering the peak plasma levels (toxic blood concentrations) and allow a systemic and tissue/organ clearance to avoid acute and chronic toxicity. Examples for such antiviral and active substances are but not limited to: Camostate® Mesylate®, Remdesivir®, Kaletra®, Foscarnet, hydroxychloroquine, Avigan®, genetic materials.

Furthermore according to the invention the combined immediate and sustained release formulation (IR and SR) of the siosomes with the encapsulated and/or entrapped active substances could be prepared as long term stable lyophilized powder which are appropriate for the further preparation of any pharmaceutically acceptable formulations not limited to the parenteral and solid formulations.

Preparation Methods According to the Invention

A further object of the invention is to provide a method for producing the carrier system characterised by mixing one or more organosilicon, sugar organosilicon compounds and/or incorporated active agents and/or linked molecules or genetic materials, selected from the group comprising: carbohydrate, lipids, amino acids, peptides, proteins, ACE-2 receptor inhibitors, inhibitors of the Lung Cell receptors, antiviral agents, antibacterial Agents, genetic materials (RNA, DNA, mRNA, siRNA), antigens, antibodies, immuno-agents, anti-inflammatory agents, antitumor agents, antivirus agents, navigation molecules, GSH, Oxidants, metal oxides (iron oxides, sodium meta-arsenide, oxoplatin), Remdesivir®, corticosteroids, Kaletra®, Avigan®, and positive strand RNA virus in solution at a pH value between 7 and 8, preferably 7.4, followed by homogenization or sonication of the mixture, followed by sterile filtration of the mixture, followed by lyophilisation. And reconstitution with puffer, isotonic sodium chloride or any appropriate solution for injection or infusion.

The subject matter of the present invention is therefore the product of the above-described method of manufacture.

Furthermore, this method according to the invention can be carried out between 37 C.° and Tc° C., or at appropriate temperature, thus facilitating the maintenance of tertiary structure of proteins and antigens, and also the activity of enzymes. The production of said carrier system complexes at such low temperatures leads to the unexpected effects of maintaining native protein structure and excellent stability. Preparation of an organosilicon carrier system under these conditions has not been described in any relevant literature to date.

The claimed method generally requires a mixing time of 40-120 minutes. This represents a significant reduction in time compared to the production of vesicles using organosilicon compounds when encapsulating any given biological agent.

The method for preparation provided by the present invention can also comprise of one or more of the following additives, including detergent solution, adjuvant solution, buffer solution, salt solution, non-cationic lipids, PEG and/or PEG-conjugates, lyosomes and/or other vesicles.

In yet another embodiment, the present invention provides a multi-targeting and delivery system for active substances, whereby coating materials of the siosomes such as poly dextrines, poly saccharide, chitosan of varying molecular weights can be used to be conjugated or covalently attached to the silicone with or without spacer and/or chemical group or covalently attached to the silicone with or without spacer and/or chemical group or covalently attached to one or more of the groups R1, R2, R3, and R4 of the general formula.

In a preferred embodiment the covalent attachment can be carried out by means of a cleavable spacer linker. and the multi-target and delivery systems are made from non-toxic/active substances and applicable for in vivo use in different therapeutics.

In the method according to the invention siosomes and/or siosomes-liposomes-complex (sio-lipo) may be encapsulated and/or entrapped with the same or different active substances and navigating molecules.

In a further preferred embodiment the composition of the multi-drug and delivery system, siosomes-liposomes complex (sio-lipo) may be administered as oral, rectal, vaginal, topical, nasal, intradermal, or parenteral, the term parenteral including subcutaneous, intravenous, intramuscular and infusion.

The method for preparing the carrier system of the present invention can also comprise of mixing the organosilicon compounds and additional biological agents in a buffer solution containing TRIS, HEPES, MOPS, MES or other commonly used biological buffer.

The organosilicon, sugar organosilicon, amino sugar organosilicon compounds, its derivatives and/or salts or vesicles thereof according to the general formula 1 are intended to be used unsolved, in water, in aqueous or organic solvent or in a solvent mixture.

The biological agents, antigens, pre-antigens, antigen conjugates, antibodies, antibody conjugates, allergens, allergen extracts, nucleic acids, plasmids, proteins, peptides, pharmaceutical agents, immunologically active substances and or cosmetics are intended to be used unsolved, in water, in aqueous or organic solvent or in a solvent mixture.

The invention also has the task of providing methods for the production of emulsions based on non-phospholipid compounds which are chemically stable, can be prepared with a defined composition, can be prepared using a method that does not disrupt protein tertiary structure, and are unaffected by factors such as high temperature and exposure to light.

The method of the present invention requires heating of the mixture to above the Tc ° C. Furthermore, no dialysis is required to remove unbound or un-encapsulated compounds, thus providing a carrier system complex of precise composition that can be easily prepared.

Sizing of the carrier system complexes may be conducted in order to achieve a desired size range and relatively narrow distribution of particle sizes. Several techniques are available for the sizing of particles to a desired size. One sizing method, used for Liposomes and equally applicable to the present invention is described in U.S. Pat. No. 4,737,323, incorporated herein by reference.

Sonicating a carrier system suspension either by bath or probe sonication produces a progressive size reduction down to particles of less than about 50 nm in size. Homogenisation is another method which relies on shearing energy to fragment larger particles into smaller ones. In a typical homogenization procedure, particles are re-circulated through a standard emulsion homogenizer until the selected particle sizes, typically between about 60 and 80 nm, are observed. In both methods the particle size distribution can be monitored by continual laser beam particle size discrimination.

Extrusion of the particles through a small pore polycarbonate membrane or an asymmetric ceramic membrane is also an effective method for reducing the particle size to a relatively well defined size distribution. Typically, the suspension is cycled through the membrane one or more times until the desired particle size distribution is achieved. The particles may be extruded though successively smaller pore membranes, to achieve a gradual reduction in size.

Lyophilisation is generally carried out using freeze drying technology controlling all aspects of the lyophilisation cycle. Sugar organosilicon or amino sugar organosilicon compounds could be used as protective compounds for dehydration and/or lyophilisation of the carrier systems.

Such sizing and subsequent lyophilisation of the carrier system complexes leads to the unexpected advantage of greater storage stability and faster rehydration before administration. Carrier complexes are stable for extended periods of time at 4-8 C.°, thus facilitating the maintenance of native protein structure during storage.

Therefore, an object of the invention is the use of the carrier system as a constituent in an immunotherapeutic for the desensitization of allergies in humans and higher animals, the use of the carrier system in the preparation of immune-therapeutics, or directly as immune-therapeutics.

Unexpected, these compounds and derivatives of the general formula (1) form surprisingly stable carrier systems and differ significantly from the siosomes and liposomes described in the prior art. Such particles have different chemical structures than those known in the prior art (table 1-9). Therefore, it is a preferred embodiment of the invention to provide specific carrier systems for the multi-targeting and delivery systems e.g. navigating molecules:

Multi-Targeting Features of the Multi-Target and Delivery Systems

As subject matter of the invention is furthermore the specific targeting of organ and tissues not limited to the GI, and CNS systems Targeting the Gastrointestinal Tract (GI) (Example 5, FIG. 6)

According to the invention the Siosomes® will have on the surface in the position 1-3 "SIO-navigators" for specific delivery and targeting of GLP-1.

According to the invention it will also be possible to design and develop Siosomes® with an "Modifier and/or Activator" for the GLP-1-Receptor "GLP-1R" so-called: SIO-GLP-1-R In this case the GLP-1 molecule will be on the surface of the Siosomes®. It means the targeting will be through the GLP-1 molecule in addition to others. (FIG. 6)

The following could be directly linked or entrapped or encapsulated:

Targeting and Penetration of the BBB (Example 5)

This multi-target and delivery siosomes system according to the invention has a number of advantages. For example the siosomes with encapsulated and/or entrapped active agents and with navigating molecules at its surface such as carbohydrates, amino acids, neurotransmitters and/or peptides could penetrate the BBB. This could have interaction with the viruses in the CNS systems which have shown the following CNS symptoms in patients infected by SARS Co-2-V:

Dizziness
Headache
Taste disorders
Disorders of the sense of smell
Stroke

Inhibition of the SARS Co-2V

Furthermore, it is a preferred embodiment of the present invention, that the multi-target siosome carrier provides a composition for the prevention, attenuation, and/or treatment of the SARS Co2-V virus and may be as well for other viruses. The following interactions will take place simultaneously between the multi-target and delivery siosomes with the human cells and virus:

Blocking of the ACE2 receptors in the host cells in the lung, kidney, heart and GI and thereby prevents the penetration of the virus into the human cells and thereby inhibit the viral infection.

Blocking the spike proteins on the surface of the SARS Co2-V (Virion). This protein as part of the virus is responsible for the contact of the virus with the ACE2 receptors in the host cell and the penetration of the virus into the host cells and thus causes the viral infection Demage the internal function of the virus, for example: inhibition of the nucleocapsid with the RNA polymerase, disruption of the Golgi apparatus and the transport of the replicated virus to the membrane. This is due to the interaction of the active substances such as antiviral inhibitors, polymerase inhibitors, amino acids, peptides, oxidants, carbohydrates which are transported into the virus/virion by the transfection of the fuse-siosomes with the encapsulated and/or entrapped active substances.

It is a preferred embodiment of the invention to provide specific carrier systems with active substances such as antiviral agents and/or monoclonal antibodies (mAbs) on the surface of the siosomes via linkers (cleavable or non-cleavable). This will enable the interactions of the antiviral agent with the virus and cause the prevention, attenuation, and/or treatment of the disease.

In yet another embodiment the empty un-encapsulated or un-entrapped siosomes or liposomes or siosomes-liposomes complexes could be used for the prevention, attenuation or treatment of the disease caused by SARS Co2-V viruses and other viruses.

In a preferred embodiment puffer solution, salts, trace elements and/or physiological solutions could be enclosed in the siosomes or liposomes or siosomes-liposomes complexes and used for the prevention, attenuation or treatment of the disease caused by SARS Co2-V viruses and other viruses.

The preferred organosilicon, sugar organosilicon, and amino sugar organosilicon and amino sugar organosilicon compounds as listed, and amino sugar organosilicon and amino sugar organosilicon compounds as listed Definition of Terms Following are exemplary definitions applicable to terms and acronyms within the detailed description. It should be understood that these definitions are only exemplary in nature and other definitions may also apply.

The following terms are defined as follows.

"Silane" is a chemical compound with the chemical formula $SiH_4$. It is the silicon analogue of methane.

"Organosilicons" are organic compounds containing carbon-silicon bonds (C—Si).

"Siloxanes" are a class of organic or inorganic chemical compounds of silicon, oxygen, and usually carbon and hydrogen, based on the structural unit $R_2SiO$, where R is an alkyl group, usually methyl.

"Siosomes" are the vesicles created from organosilicon compounds with hydrophilic and hydrophobic ends. Siosomes consist of at least one concentric, self-contained layer of organosilicon compounds with the organosilicon general structure. An aqueous compartment is enclosed by the bimolecular organosilicon membrane.

"Sugar-siosomes" refer to siosomes consisting of sugar organosilicon compounds.

As used herein in this patent "blank siosomes" refers to any and all vesicles prepared from organosilicon compounds without encapsulated and/or entrapped pharmacologically and/or immunologically active agents. Specific examples of "blank siosomes" are siosomes filled with water, salts or buffer.

"Siosome-entrapped active substance" Entrapped in the siosomes is an active substance for intracellular delivery to the target cells. A variety of active substances can be entrapped in siosome vesicles, including water soluble agents, for example small water soluble organic compounds, peptides, proteins, DNA plasmids, oligonucleotides, and gene fragments, which can be stably encapsulated in the aqueous compartment of the siosomes. Furthermore, lipophilic compounds that stably partition in the lipid phase of the siosomes, or agents that can be stably attached, for example by electrostatic attachment to the outer siosome surfaces, are also intended.

According to the invention the following compounds and active agents will be encapsulated, entrapped, conjugated and/or linked using cleavable or un-cleavable linkers: Carbohydrate, lipid, amino acids, peptides, proteins, ACE-2 receptor inhibitors, Inhibitors of the Lung Cell receptors, antiviral agents, antibacterial agents, genetic materials (RNA, DNA, mRNA, siRNA), antigens, antibodies, immuno-agents, anti-inflammatory agents, antitumor agents, antivirus agents, navigation molecules, GSH, Oxidants, metal oxides (iron oxides, sodium meta-arsenide, oxoplatin), Remdesivir, corticosteroids, Kaletra, Avigan, positive strand RNA virus, and sodium meta-arsenite.

"Liposomes" are the vesicles created from phospholipids. Liposomes consist of at least one concentric, self-contained layer of phospholipids and an aqueous compartment enclosed by the bimolecular phospholipid membrane.

"Tc: Transition Temperature of The Lipid" as used herein in this patent is the phase transition temperature and is defined as the temperature required to induce a change in the lipid physical state from the ordered gel phase, where the hydrocarbon chains are fully extended and closely packed, to the disordered liquid crystalline phase, where the hydrocarbon chains are randomly oriented and fluid. There are several factors which directly affect the phase transition temperature including hydrocarbon length, unsaturation, charge, and head group species. As the hydrocarbon length is increased, van der Waals interactions become stronger requiring more energy to disrupt the ordered packing, thus the phase transition temperature increases. Likewise, introducing a cis double bond into the acyl group puts a kink in the chain which requires much lower temperatures to induce an ordered packing arrangement "Encapsulations" are to be understood as the capture by a siosome or liposome of a dissolved hydrophilic solute within the region of aqueous solution inside a hydrophobic membrane, whereby the dissolved hydrophilic solutes cannot readily pass through the lipid bi-layer.

"Entrapments" are to be understood as the capture by a liposome or siosome of hydrophobic solutes dissolved in the hydrophobic region of the bi-layer membrane.

"Glucagon-like peptide-1 (GLP-1)" is a 30 or 31 amino acid long peptide hormone deriving from the tissue-specific posttranslational processing of the proglucagon peptide. It is produced and secreted by intestinal enteroendocrine L-cells and certain neurons within the nucleus of the solitary tract in the brainstem upon food consumption.

"Glucagon" is a hormone that raises the level of glucose (a type of sugar) in the blood. The pancreas produces glucagon and releases it when the body needs more sugar in the blood for delivery to the cells.

"Virion, are to be understood as a complete viral particle, consisting of RNA or DNA surrounded by a protein shell and constituting the infective form of a virus.

"Monoclonal antibodies (mAb or moAb" are antibodies that are made by identical immune cells that are all clones of a unique parent cell. Monoclonal antibodies can have monovalent affinity, in that they bind to the same epitope (the part of an antigen that is recognized by the antibody).

"Combinations" or "complex combinations" of the present invention are intended to be understood as complexes formed between the organosilicon, sugar organosilicon, amino sugar organosilicon compounds, their derivatives, salts and/or the vesicles formed from them, with the biological agents, selected from antigens, pre-antigens, antigen conjugates, antibodies, antibody conjugates, allergens, allergen extracts, nucleic acids, plasmids, proteins, peptides, pharmaceutical agents, immunologically active substances and/or cosmetics, whereby the complexes are held together via the sum force of non-covalent bonds including Hydrophobic interactions between non-polar regions, such as the hydrophobic fatty acid chains of the organosilicon, sugar organosilicon, amino sugar organosilicon compounds and siosomes, non-specific protein-protein interactions between protein segments of an allergen and/or the peptide residues of the organosilicon, sugar organosilicon, amino sugar organosilicon compounds, protein-saccharide interactions, Van der Waals interactions including, dipole-dipole interactions, dipole-induced dipole interactions, dispersion forces (London forces), electrostatic interactions between charged resides, for example peptide residues and organosilicon, sugar organosilicon, amino sugar organosilicon compounds, and salts, ion-dipole forces; for example those between the salts of the buffer used in the preparation of the complex and $H_2O$, and ion-ion forces; for example those involving the salts of the buffer solution.

An "antigen" is to be understood as a substance that prompts the generation of antibodies and can cause an immune response.

A "pre-antigen" is to be understood as an antigen in an inactive state prior to processing to the active form.

An "antigen conjugate" is to be understood as an antigen conjugated covalently to another biological agent, such as an enzyme or other protein.

An "antibody conjugate" is to be understood as an antibody conjugated covalently to another biological agent, such as an enzyme or other protein.

The term "allergen" refers to a substance, protein or non-protein, capable of inducing allergy or specific hypersensitivity or an extract of any substance known to cause allergy. The term "allergen extract" refers to a natural extract of multiple allergens, protein or non-protein, capable of inducing allergy or specific hypersensitivity or an extract of any substance known to cause allergy.

A "pharmaceutical agent" is to be understood as any medicament, intended for use in the diagnosis, cure, mitigation, treatment, or prevention of disease in humans or animals.

"Human cytomegalovirus structure" consists of an outer lipid bilayer envelope, composed of various viral glycoproteins, followed by the tegument, a proteinaceous matrix, which holds double stranded linear DNA core in an icosahedral nucleocapsid. The virion is usually spherical in composition.

"The influenza virion" (as the infectious particle is called) is roughly spherical. It is an enveloped virus—that is, the outer layer is a lipid membrane which is taken from the host cell in which the virus multiplies. Inserted into the lipid membrane are 'spikes', which are proteins—actually glycoproteins, because they consist of protein linked to sugars—known as HA (hemagglutinin) and NA (neuraminidase). These are the proteins that determine the subtype of influenza virus (A/H1N1, for example).

"Vaccinia virus (VACV or VV)" is a large, complex, enveloped virus belonging to the poxvirus family. It has a linear, double-stranded DNA genome approximately 190 kbp in length, which encodes approximately 250 genes. The dimensions of the virion are roughly 360×270×250 nm, with a mass of approximately 5-10 fg.

An "immunologically active substance" is to be understood as any substance that leads to an immune response in a human or animal patient.

As used herein "sugar" includes any and all monosaccharide, disaccharide, polysaccharide, amino-sugar or hydroxyl carbon acid, it's derivatives, salts and/or residues remaining after the removal of a hydrogen atom from it. The following are suitable examples of suitable monosaccharides; pentoses such as arabinose, ribose and xylose as well as hexoses such as glucose, mannose, galactose and fructose. Suitable amino sugars include e.g. glucosamin and galactosamin. A suitable carbon acid for example is glucronic acid. The hydroxyl carbon acids' hydroxyl groups can be free, partially derivatized or fully derivatized (protective groups) specific examples of amino sugar silicon compounds are listed herein.

A "patient" for the purposes of the present invention includes both humans and other animals, particularly mammals, and other organisms. Thus the methods are applicable to both human therapy, vaccinations, and veterinary applications. In the preferred embodiment the patient is a mammal, the most preferred being a human.

The term "animal" refers to an organism with a closed circulatory system of blood vessels and includes birds, mammals and crocodiles. The term "animal" used here also includes human subjects.

An "immunologically effective amount" is the quantity of a compound, composition or carrier system of the present invention which is effective in yielding the desired immunologic response.

The terms "treating cancer," "therapy," and the like refer generally to any improvement in the mammal having the cancer wherein the improvement can be ascribed to treatment with the compounds of the present invention. The improvement can be either subjective or objective.

Accordingly, the carrier systems of the invention are administered to cells, tissues, healthy volunteers and subjects and/or patients. Herein what is meant by "administered" is the administration of a therapeutically effective dose of the candidate agents of the invention to a cell either in cell culture or in a patient. Herein what is meant by "therapeutically effective dose" is a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. Herein what is meant by "cells" is almost any cell in which mitosis or miosis can be altered.

Additional "carriers" may be used in the "carrier system" of the present invention, and include any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the carrier systems.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectable, either as liquid solutions or suspensions; solid forms suitable for solution in, or suspension in, liquid prior to injection can also be prepared. The preparation can also be emulsified.

The term "pharmaceutically acceptable salt" refers to those salts of compounds which retain the biological effectiveness and properties of the free bases and which are obtained by reaction with inorganic acids such as hydrochloric acid, hydrobromic acid, sulphuric acid, nitric acid, phosphoric acid, methanesulphonic acid, ethanesulphonic acid, toluenesulphonic acid, salicylic acid and the like. Pharmaceutically acceptable salts include alkali metal salts, such as sodium and potassium, alkaline earth salts and ammonium salts.

Therefore, as used herein, "cancer" refers to all types of cancer or neoplasm or malignant tumours found in mammals, including carcinomas and sarcomas. Examples of cancers are cancer of the brain, breast, cervix, colon, head & neck, kidney, lung, non-small cell lung, melanoma, mesothelioma, ovary, sarcoma, stomach, and uterus.

The present invention relates to the use of organosilicon, sugar organosilicon, amino sugar organosilicon compounds, their derivatives, salts and/or the vesicles formed from them in a carrier system with antigens, pre-antigens, antigen conjugates, antibodies, antibody conjugates, allergens, allergen extracts, nucleic acids, plasmids, proteins, peptides, pharmaceutical agents, immunologically active substances and/or cosmetics, for the manufacturing of a pharmaceutical, immunological and/or cosmetic composition for the different indications.

The "pharmaceutical composition" of the invention optionally comprises of one or more pharmaceutically acceptable adjuvants, excipients, carriers, buffers, diluents and/or customary pharmaceutical auxiliary substances. The composition of the invention is administered in a pharmaceutically acceptable formulation. The present invention pertains to any pharmaceutically acceptable formulations, such as synthetic or natural polymers in the form of macromolecular complexes, nanocapsules, microspheres, or beads, and lipid-based formulations including oil-in-water emulsions, micelles, mixed micelles, synthetic membrane vesicles, and resealed erythrocytes. In addition to the said composition and the pharmaceutically acceptable polymer, the pharmaceutically acceptable formulation of the invention can comprise additional pharmaceutically acceptable carriers and/or excipients. As used herein, a pharmaceutically acceptable carrier includes any and all solvents, dispersion media, coatings, antibacterial and anti fungal agents, isotonic and absorption delaying agents, and the like that are physiologically compatible. For example, the carrier can be suitable for injection into the cell, tissues, organs and/or blood. Excipients include pharmaceutically acceptable stabilizers and disintegrants. In another embodiment, the pharmaceutically acceptable formulations comprise lipid-based formulations. Any of the known lipid-based drug delivery systems can be used in the practice of the invention. For instance, multivesicular liposomes (MVL), multilamellar liposomes (also known as multilamellar vesicles or MLV), unilamellar liposomes, including small unilamellar liposomes (also known as unilamellar vesicles or SUV), large unilamellar liposomes (also known as large unilamellar vesicles or LUV), multivesicular siosomes (MVS), multilamellar siosomes (MLS), unilamellar siosomes including small unilamellar siosomes can all be used so long as a sustained release rate of the carrier system composition of the invention can be established.

In one embodiment, the lipid-based formulation can be a multivesicular liposome system. Other phospholipids or other lipids may also be used. Examples of lipids useful in synthetic membrane vesicle production include phosphatidylglycerols, phosphatidylcholines, phosphate-idylserines, phosphatidyl-ethanolaminos, sphingolipids, cerebrosides, and gangliosides. Preferably phospholipids including egg phosphatidylcholine, dipalmitoylphosphat-idylcholine, distearoylphosphatidylcholine, dioleoylphos-phatidylcholine, dipalmitoylphosphatidylglycerol, and dioleoylphosphatidylglycerol are used. In another embodiment, the composition containing the carrier system of the invention may be incorporated or impregnated into a bioabsorbable matrix. In addition, the matrix may be comprised of a biopolymer. A suitable biopolymer for the present invention can include also one or more macromolecules selected from the group consisting of collagen, elastin, fibronectin, vitronectin, laminin, polyglycolic acid, hyaluronic acid, chondroitin sulphate, dermatan sulphate, heparin sulphate, heparin, fibrin, cellulose, gelatine, polylysine, echinonectin, entactin, thrombospondin, uvomorulin, biglycan, decorin, and dextran. The formulation of these macromolecules into a biopolymer is well known in the art. In a preferred embodiment, the therapeutic composition is not immunogenic when administered to a human patient for therapeutic purposes.

A "pharmaceutical carrier system" according to the invention may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anaesthetics, antianginals, antifungals, antibiotics, anti-cancer drugs (e.g., taxol or mitomycin C), anti-inflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antipsychotics, antipyretics, antiseptics, anti-signalling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympatho-mimetics, sedatives, stimulants, sympathomimetics, toxins (e.g., cholera toxin), tranquilizers and urinary anti-infectives, to amino acids, peptides, proteins, ACE-2 receptor inhibitors, Inhibitors of the Lung Cell, receptors, antiviral agents, antibacterial Agents, genetic materials (RNA, DNA, mRNA, siRNA), antigens, antibodies, immuno-agents, anti-inflammatory agents, antitumor agents, antivirus agents, navigation molecules, GSH, Oxidants, metal oxides (iron oxides, sodium meta-arsenide, oxoplatin).

The "pharmaceutical carrier systems" for administration to patients, the active substances of the present invention are mixed with a pharmaceutically acceptable carrier or diluent in accordance with routine procedures. Therapeutic and/or immunologic formulations will be administered by intravenous infusion or by subcutaneous injection. The formulations can also contain, if desired, other therapeutic agents.

The invention relates also to a process or a method for the treatment of the abovementioned pathological conditions. The compounds of the present invention can be administered prophylactically or therapeutically, preferably in an amount that is effective against the mentioned disorders, to a warm-blooded animal, for example a human, requiring such treatment, the compounds preferably being used in the form of pharmaceutical carrier systems.

In certain embodiments, the inventors contemplate the use of nanocapsules, microparticles, microspheres, and the like, in the production of the carrier systems of the present invention. Such formulations may be preferred for the introduction of pharmaceutically-acceptable formulations of the carrier system or constructs disclosed herein.

The invention provides for pharmaceutically-acceptable nanocapsule formulations of the carrier systems of the present invention. Nanocapsules can generally entrap compounds in a stable and reproducible way. To avoid side effects due to intracellular polymeric overloading, such ultra fine particles should be designed using polymers able to be degraded in vivo. Biodegradable polyalkyl-cyanoacrylate nanoparticles that meet these requirements are contemplated for use in the present invention.

"Lung epithelial cells" according to the invention are increasingly recognized to be active effectors of microbial defense, contributing to both innate and adaptive immune function in the lower respiratory tract. As immune sentinels, lung epithelial cells detect diverse pathogens through an ample repertoire of membrane-bound, endosomal, and cytosolic pattern-recognition receptors (PRRs)

"Angiotensin converting enzyme 2 (ACE2)" according to the invention is a zinc carboxypeptidase involved in the renin-angiotensin system (RAS) and inactivates the potent vasopressive peptide angiotensin II (Ang II) by removing the C-terminal phenylalanine residue to yield Ang1-7. This conversion inactivates the vasoconstrictive action of Ang II and yields a peptide that acts as a vasodilatory molecule at the Mas receptor and potentially other receptors. Given the growing complexity of RAS.

The localization of ACE2 protein in various human organs (oral and nasal mucosa, nasopharynx, lung, stomach, small intestine, colon, skin, lymph nodes, thymus, bone marrow, spleen, liver, kidney, and brain) have been investigated. The most remarkable finding was the surface expression of ACE2 protein on lung alveolar epithelial cells and enterocytes of the small intestine. Furthermore, ACE2 was present in arterial and venous endothelial cells and arterial smooth muscle cells in all organs studied. In conclusion, ACE2 is abundantly present in humans in the epithelia of the lung and small intestine, which might provide possible routes of entry for the SARS-CoV.

"Spike protein (S) of SARS coronavirus (SARS-CoV)" according to the invention attaches the virus to its cellular receptor, angiotensin-converting enzyme 2 (ACE2). A defined receptor-binding domain (RBD) on S mediates this interaction. The crystal structure at 2.9 angstrom resolution of the RBD bound with the peptidase domain of human ACE2 shows that the RBD presents a gently concave surface, which cradles the N-terminal lobe of the peptidase. The atomic details at the interface between the two proteins clarify the importance of residue changes that facilitate efficient cross-species infection and human-to-human transmission. The structure of the RBD suggests ways to make truncated disulfide-stabilized RBD variants for use in the design of coronavirus vaccines.

"RNA-dependent RNA polymerase (RdRp, also named nsp12)" according to the invention is the central component of coronaviral replication/transcription machinery and appears to be a primary target for the antiviral drug, Remdesivir.

"TLRs" according to the invention are the receptors in the lung and include transmembrane molecules such as the toll-like receptors (TLRs)
   protease-activated receptors (PARs)
   purinergic receptors
   cytosolic proteins including the nucleotide-binding, leucine-rich repeat receptors (NLRs)
   retinoic acid-inducible gene I-like helicases (RLHs]

"Protein Transmembrane protease serine 2—Gene TMPRSS2" according to the invention: Serine protease that proteolytically cleaves and activates the viral spike glycoproteins which facilitate virus-cell membrane fusions; spike proteins are synthesized and maintained in precursor intermediate folding states and proteolysis permits the refolding and energy release required to create stable virus-cell linkages and membrane coalescence. Facilitates human SARS coronavirus (SARS-CoV) infection via two independent mechanisms, proteolytic cleavage of ACE2, which might promote viral uptake, and cleavage of coronavirus spike glycoprotein which activates the glycoprotein for cathepsin L-independent host cell entry. Proteolytically cleaves and activates the spike glycoproteins of human coronavirus 229E (HCoV-229E) and human coronavirus EMC (HCoV-EMC) and the fusion glycoproteins F0 of Sendai virus (SeV), human metapneumovirus (HMPV), human parainfluenza 1, 2, 3, 4a and 4b viruses (HPIV). Essential for spread and pathogenesis of influenza A virus (strains H1N1, H3N2 and H7N9); involved in proteolytic cleavage and activation of hemagglutinin (HA) protein which is essential for viral infectivity.

"SARS" according to the invention stands for severe acute respiratory syndrome. In 2003, an outbreak of SARS started in China and spread to other countries before ending in 2004. The virus that causes COVID-19 is similar to the one that caused the 2003 SARS outbreak: both are types of coronaviruses. Much is still unknown, but COVID-19 seems to spread faster than the 2003 SARS.

"COVID 19" according to the invention as Corona Virus Disease 2019 as a mild to severe respiratory illness that is caused by a coronavirus (Severe acute respiratory syndrome coronavirus 2 of the genus Betacoronavirus), is transmitted chiefly by contact with infectious material (such as respiratory droplets), and is characterized especially by fever, cough, and shortness of breath and may progress to pneumonia and respiratory failure.

"Protease" for the purpose of the present invention is any of numerous enzymes that hydrolyze proteins and are classified according to the most prominent functional group (such as serine or cysteine) at the active site.

"Protease inhibitor" is to be understood as a substance that inhibits the action of a protease specifically: any of various drugs (such as indinavir) that inhibit the action of the protease of HIV so that the cleavage of viral proteins into mature functional infectious particles is prevented and that are used especially in combination with other agents in the treatment of HIV infection.

"Antiviral drugs" according to the invention act against diseases caused by viruses.

"Antibacterial drugs" means it can kill bacteria or slow their growth.

"Anti-inflammatory agents" according to the invention as drugs acting to reduce certain signs of inflammation, as swelling, tenderness, fever, and pain.

"RNA polymerase" (RNAP or RNA pol) is according to the invention is an enzyme that is responsible for making rna from a dna template. In all cells RNAP is needed for constructing ma chains from a dna template, a process termed transcription. In scientific terms, RNAP is a nucleotidyl transferase that polymerizes ribonucleotides at the 3' end of an ma transcript. Rna polymerase enzymes are essential and are found in all organisms, cells, and many viruses.

"Transfection" according to the invention is to be understood as Introduction of a segment of DNA or RNA into a eukaryotic cell by means of one of a variety of physical or chemical methods or through viral infection.

Or the introduction of the organosilicon nanoparticle in the SARS-CoV2 virus and any SARS viruses to inhibit the virus.

"Chemical Transfection agents" for the purpose of the present invention Transfection overcomes the inherent challenge of introducing negatively charged molecules (e.g., phosphate backbones of DNA and RNA) into cells with a negatively charged membrane. Chemicals like calcium phosphate and diethylaminoethyl (DEAE)-dextran or cationic lipid-based reagents coat the DNA, neutralizing or even imparting an overall positive charge to the molecule. This process makes it easier for the DNA:transfection reagent complex to cross the membrane, especially for lipids that have a "fusogenic" component, which enhances fusion with the lipid bilayer. Chemical methods neutralize the negative charge of DNA, facilitating its uptake. Lipid-based reagents can also coat DNA while forming micelles. Electroporation makes the membrane more permeable transiently, allowing DNA to enter the cell.

Organosilicon nanoparticles according to this invention has positively charged membrane due to the positive charged silicon atoms and it is considered as cationic lipid based reagent "Navigating molecules/navigators" is for the purpose of the invention They are molecules on the surface of the siosomes and are specific for certain tissues and or cells.

They guide the siosomes with the encapsulated and or entrapped active ingredients to the organs or cells of interest. As example are the neurotransmitter to target the organo-silicon siosomes nano particles to the brain.

"Genetic materials" of a cell or an organism refers to those materials found in the nucleus, mitochondria and cytoplasm, which play a fundamental role in determining the structure and nature of cell substances, and capable of self-propagating and variation.

In addition the genetic material of a cell can be a gene, a part of a gene, a group of genes, a DNA molecule, a fragment of DNA, a group of DNA molecules, or the entire genome of an organism.

"Positive-strand RNA virus": Also known as a sense-strand RNA virus, a virus whose genetic information consists of a single strand of RNA that is the positive (or sense) strand which encodes mRNA (messenger RNA) and protein. Replication in positive-strand RNA viruses is via a negative-strand intermediate. Examples of positive-strand RNA viruses include polio virus, Coxsackie virus, and echovirus.

There are two types of RNA viruses. Some are positive in that they have a "sense" strand of RNA (coded information about how to build proteins) as their genetic material. And other RNA viruses tare negative in that they have an "antisense" strand (the paired opposite of the coded information). Positive-strand or sense-strand RNA viruses are therefore as opposed to negative-strand or antisense-strand RNA viruses.

"Captopril" according to the invention is a sulfhydryl-containing analog of proline with antihypertensive activity and potential antineoplastic activity. Captopril competitively inhibits angiotensin converting enzyme (ACE), thereby decreasing levels of angiotensin II, increasing plasma renin activity, and decreasing aldosterone secretion "Camostat® mesylate" according to the invention as orally active protease inhibitor; inhibits entry of SARS-CoV-2 into lung cells. It inhibits trypsin and various inflammatory proteases including plasmin, kallikrein and thrombin. Also inhibits transmembrane serine protease TMPRSS2 and partially blocks entry of SARS-CoV-2 (COVID-19) into lung cells in vitro.

"Remdesivir®" for the purpose of the present invention is a prodrug that metabolizes into its active form GS-441524. An adenosine nucleotide analog, GS-441524 interferes with the action of viral RNA-dependent RNA polymerase and evades proofreading by viral exoribonuclease (ExoN), causing a decrease in viral RNA production. It was unknown whether it terminates RNA chains or causes mutations in them. [4] However, it has been learned that the RNA-dependent RNA polymerase of Ebola virus is inhibited for the most part by delayed chain termination. [31].

"KALETRA®" (lopinavir and ritonavir)" to be understood as a co-formulation of lopinavir and ritonavir. Lopinavir is an inhibitor of the HIV-1 protease. As co-formulated in KALETRA ritonavir inhibits the CYP3A-mediated metabolism of lopinavir, thereby providing increased plasma levels of lopinavir.

"AVIGAN®" (Favipiravir) according to the invention as antiviral drug being developed by Toyama Chemical (Fujifilm group) of Japan with many activity against many RNA viruses. The mechanism of its actions is thought to be related to the selective inhibition of viral RNA-dependent RNA polymerase. Other research suggests that favipiravir induces lethal RNA transversion mutations producing a nonviable viral phenotype.

"Corticosteroids" according to the invention Corticosteroids are a class of steroid hormones released by the adrenal cortex, which includes glucocorticoids and mineralocorticoidsl. However, the term "corticosteroids" is generally used to refer to glucocorticoids. Named for their effect in carbohydrate metabolism, glucocorticoids regulate diverse cellular functions including development, homeostasis, metabolism, cognition and inflammation2. Due to their profound immune-modulatory actions, glucocorticoids are one of the most widely prescribed drugs in the world. and t Glucocorticoids have become a clinical mainstay for the treatment of numerous inflammatory and autoimmune diseases, such as asthma, allergy, septic shock rheumatoid arthritis, inflammatory bowel disease, and multiple sclerosis.

"Gluthation GSH" for the purpose of the present invention is as a tripeptide with many roles in cells. It conjugates to drugs to make them more soluble for excretion, is a cofactor for some enzymes, is involved in protein disulfide bond rearrangement and reduces peroxides.

"Chloroquine Phosphate" is the phosphate salt of chloroquine, a quinoline compound with antimalarial and anti-inflammatory properties. Chloroquine is the most widely used drug against malaria, except for those cases caused by chloroquine resistant *Plasmodium falciparum*. Although the mechanism of action is not fully understood, chloroquine is shown to inhibit the parasitic enzyme heme polymerase that converts the toxic heme into non-toxic hemazoin, thereby resulting in the accumulation of toxic heme within the parasite. Chloroquine may also interfere with the biosynthesis of nucleic acids.

"Hydroxychloroquine" is a 4-aminoquinoline with immunosuppressive, antiautophagy, and antimalarial activities. Although the precise mechanism of action is unknown, hydroxychloroquine may suppress immune function by interfering with the processing and presentation of antigens and the production of cytokines. As a lysosomotropic agent, hydroxychloroquine raises intralysosomal pH, impairing autophagic protein degradation; hydroxychloroquine-mediated accumulation of ineffective autophagosomes may result in cell death in tumor cells reliant on autophagy for survival. In addition, this agent is highly active against the erythrocytic forms of *P. vivax* and malariae and most strains of *P. falciparum* but not the gametocytes of *P. falciparum*.

"Sodium Metaarsenite" is a highly soluble, orally available trivalent arsenic-containing telomerase inhibitor with potential antitumor activity. Although the exact mechanism through which sodium metaarsenite exerts its effect has yet to be fully elucidated, this agent appears to target and bind to telomeric sequences, specifically TTAGGG repeats, leading to a shortening of telomeres, and subsequent induction of apoptosis and inhibition of tumour cell growth. In addition, sodium metaarsenite also leads to the translocation of the catalytic subunit of telomerase into the cytoplasm and inhibition of the activity of telomerase. Telomerase is active in most tumors cells and is responsible for the maintenance of telomere length and plays a key role in cellular proliferation, but is quiescent in normal, healthy cells. The susceptibility to sodium meta-arsenite seems to be inversely correlated with initial length of telomeres.

"Blocker" for the purpose of the present invention is as a substance which prevents or inhibits a given physiological function, or a drug or other substance that prevents certain biochemical reaction, or to interrupt or obstruct the functioning of a physiological process, especially by the use of drugs.

"Neurotransmitter" for the purpose of the present invention is as a chemical substance which is released at the end of a nerve fibre by the arrival of a nerve impulse and, by diffusing across the synapse or junction, effects the transfer of the impulse to another nerve fibre, a muscle fibre, or some other structure.

"Siosomes transfection agents" according to the invention is to be understood as siosomes (Si—R1, R2, R3, R4) whereby one or more of the residues R1, R2, R3, R4 is an cationic lipid.

Description of the Preferred Advantages of the Invention

The importance of Sugar-Siosomes according to the invention is to provide multi-targeting and delivery system for the treatment, attenuation and/or prevention of inflammation caused by the SARS viruses A number of Sugar-Silanes made into siosomes in this invention have been designed and prepared for screening of the antiviral and anticancer activities. These sugar residues are glucose, galactose, mannose and other saccharides. The importance and relevance are as follows;

The Siosomes membrane has been designed according to the invention to mimic biomembranes with lipid layers and sugar molecules Accumulating research evidence suggests that in many cases carbohydrates (frequently referred to as sugars) are the primary markers for cell recognition and communication. Discoveries about the involvement of specific sugars in recognition will have practical applications to the prevention and treatment of a variety of ailments, including cancer and viral infections;

In addition, research development has shown that:

All cells carry a sugar coat. This coat consists for the most part of glycoproteins and glycolipids, two types of complex carbohydrates in which sugar are linked to proteins and lipids (fats), respectively. Several thousands of glycoproteins and glycolipids structures have been identified, and their number grows almost daily. This diversity is surely significant: the repertoire of surface structures on a cell changes characteristically as it develops, differentiates or sickens. The array of carbohydrates on cancer cells is strikingly different from that in viruses and normal one.

Lectins—a class of proteins that can combine with sugars rapidly, selectively and reversibly.

Lectins frequently appear on the surfaces of cells, where they are strategically positioned to combine with carbohydrate on neighbouring cells. They demonstrate quite specificity: lectins distinguish not only between different monosaccharides but also between different oligosaccharides.

To cause disease, viruses, bacteria or protozoa must able to stick to at least one tissue surface in a susceptible host. Infectious agents lacking that ability are swept away from potential site of infection by the body's normal cleansing mechanisms;

Considerable experimental evidence now greatly strengthens the conclusion that the binding of bacteria to host cell-surface sugars initiates infection;

In theory any drug that interferes with the adhesion of white blood cells to the endothelium, and consequently with their exit from the blood vessel, should be anti-inflammatory;

For an anti-adhesive therapy to be successful, the drugs must simultaneously accomplish two seemingly incompatible ends;

These characteristics above according to the invention allow the attractiveness of using Sugar-Siosomes for drug targeting and delivery.

The sugar molecules in the surface of the siosomes and/or encapsulated, entrapped and/or conjugated in the siosomes will have the following functions:
1) Navigate the multitarget systems according to module 1 of the invention to the ACE2-receptor at the cell in the host and block and/or inhibit the ACE2 receptor and prevent the spike protein (s) of the SARS Co2-V from the interaction with the receptor and infect the cell. (FIG. 1).
2) Navigate and target the binding of the multitarget systems according to module 2 of the invention against the spike protein (s) of the SARS Co2-V. This will lead to the blocking and/or inhibition of the spike protein (s) and the virus accordingly. (FIG. 2)
3) Navigate, target and transfect the virion of the SARS Co2-V according to module 3 of the present invention. This will block, interact, change and/or inhibit the internal compartments of the virion in the SARS Co2-V (e.g. RNA-protein nucleocapsid, membrane protein). In addition blocking late stage of virus assembly) using in siosomes encapsulated, entrapped and/or conjugated polymerase inhibitors and siosomes and transfection agents. (FIG. 3)
4) Navigate the targeted binding against the sugar molecules on the surface of the virus. The interactions between the membranes of the virus and the siosomes particles will result in the fusion between them and the inhibition of the virus. (FIG. 4). Therefore as preferred embodiment of this invention is an multi-target and delivery system, whereby R1, R2, R3, are the same or different sugars (on the surface of the siosomes) and R4 is a lipid and encapsulated and/or entrapped sugar molecules in the siosomes.

In addition the advantages of Siosomes® use according to the present invention as a Carrier and Multiple Drug Targeting System sind:

Improve drug solubility for sparingly soluble compounds;
Control delivery of small molecules, peptides, proteins and nucleic acids;
Increase drug bioavailability at the disease site;
Control of bioavailability of small molecules and peptides following localized administration e.g. to the lungs, subcutaneous tissue or brain;

The lipid base formulation according to the invention may also protect active compounds from biological degradation or transformations that in turn can lead to enhancement of drug potency; reduce the toxicity of various drugs by targeting the bio-distribution of the drug to the pathological sites and away from the sensitive organs, thereby reducing the accumulation in the heart, kidney and muscle while maintaining or improving the efficacy of the active compound;

There are numerous examples where molecules such as nucleic acids, recombinant proteins, peptides as well as small molecular weight drug candidates exhibit in liposomes stability in biological fluids that is several orders of magnitude greater than the free molecule. This protection of the active molecule can lead to a significant increase on bioavailability. Siosomes® are very stable in light and at relatively high temperature, which is not the case for liposomes.

A further aspect of the present invention is the use of the multi-target and targeting systems, the siosomes for a number of specific applications e.g. for the targeting and chemical transfection of the virus for the delivery and multiple targeting of API's and active compounds such as:
1. Use of multilamellar Siosomes® vesicles which reach the site of action with at least one intact vesicle layer and still contain the active substance. (FIG. 7)
2. Use of multilamellar Siosomes® vesicles which reach the site of action with at least one intact vesicle layer and still contain the free Pro-drug polymer complex. (FIG. 8)

Possible Constructs of the Multi-Target and Delivery Siosomes According to the Invention Over 50 different silane and sugar silanes that contribute to a great diversity of functional groups have been manufactured and used for the encapsulation of active agents. However by changing the functional groups of the silanes and sugar silanes molecules, different lipid groups, linked protein molecules and different peptides, antigens, antibodies, proteins and nucleosides, this can provide limitless Siosomes constructs.

Mono-lamellar Siosomes: Can be used to encapsulate and/or entrap water, Q10, Vitamin E, sphingosine, aloe vera, collagen, hyaluronic acid, heparin etc. These applications may vary from therapeutic to cosmetics.

Multi-lamellar Siosomes: The use of Siosomes, such as multi-lamellar vesicles (MLV), which is a kind of sustained release system, provide a possibility of overcoming physiological and enzymatic barriers intact. Here, several vesicles layers protect the encapsulated active substance from being released. Further possibilities of a protected active substance transport involve the encapsulation/entrapment of pro-drug, polymer complex, pro-drug-polymer complex.

Encapsulated drug Substances: a number of active agent with different molecular structures and physicochemical properties (solubility, stability in light, PH in water) such as Propanolol, Nifedipine, Dithranol, Foscarnet, Salicilic Acid, Cis-Oxoplatin, Sodium Meta Arsenite, Arsenic Trioxide, Insulin, and Polypeptide have been successfully encapsulated in Siosomes.

Labelled Lipid Siosomes: Lipids can be conjugated on Silanes and Sugar Silanes and when Siosomes are formed the outer surface of the Siosomes may have specific lipids to enhance the skin and/or cell penetration.

Genetic materials encapsulated, entrapped or formed complex with the Siosomes

Genetic materials such as mRNAs and siRNAs can form complexes with Siosomes for intracellular delivery. A number of procedures have been developed to achieve efficient transfection.

PEGylated Siosomes: a number of PEGylated Silanes and Sugar Silanes such PEGylatedcationic, anionic and zwitterionic Silanes and Siosomes have been designed and developed for the encapsulation, entrapment and/or complex formation with active agents such as Doxorubicin and Docetaxel.

Immuno-Siosomes: The molecular structure of specific sugar silanes are appropriate for the covalent coupling of Antigens, Antibodies and proteins for the development of specific vaccines. (FIG. 5)

BRIEF DESCRIPTION OF THE DRAWINGS

FIG. 2: Inhibition of the SARS-Co2 V: Blocking the spike(s) structural proteins with the effectors on the outer layer of the siosomes.

Figure 4:
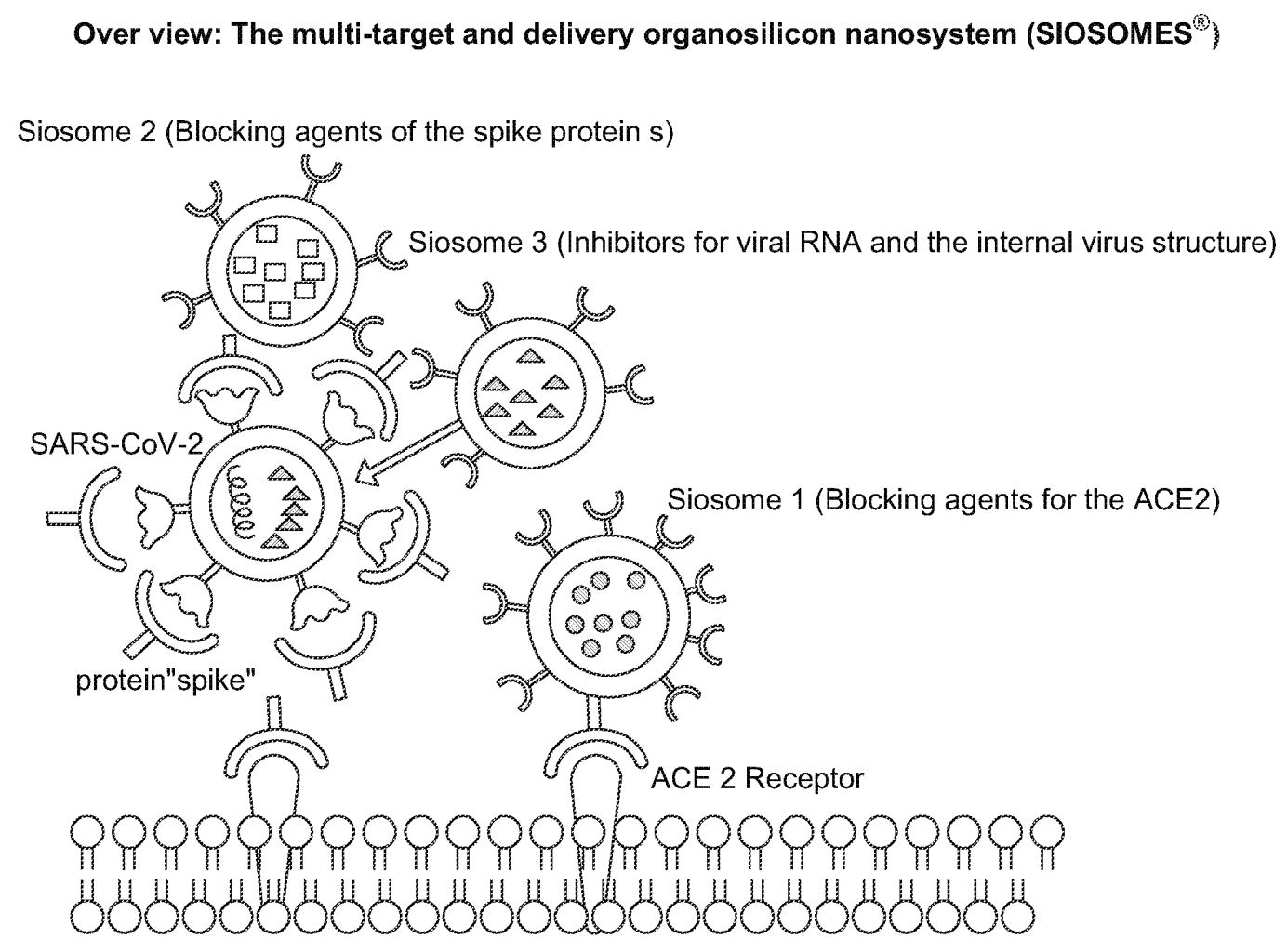

FIG. 4: Overview: the multi-target and delivery organosilicon nanosystem (Siosomes®).

FIG. 5: Structures of silanes/siosomes models with the different functions to provide a novel multi-target and delivery organosilicon siosomes nanosystem.

FIG. 12: The Siosomes-Drug conjugation (SDC) and Antibody Siosomes conjugates (ASC)—Using Linkers (cleavable/non-cleavable).

FIG. 13: The Siosomes-Genetic Material-Conjugate (SGMC and Siosomes-Antiviral Drugs-Conjugates (SADC)-Using Linkers (cleavable/non-cleavable).

FIG. 15: Preparation of the combined multi-target and delivery siosomes for the attenuation, prevention and/or treatment of the infection caused by the SARS Co 2V.

EXAMPLES

Figure 1:
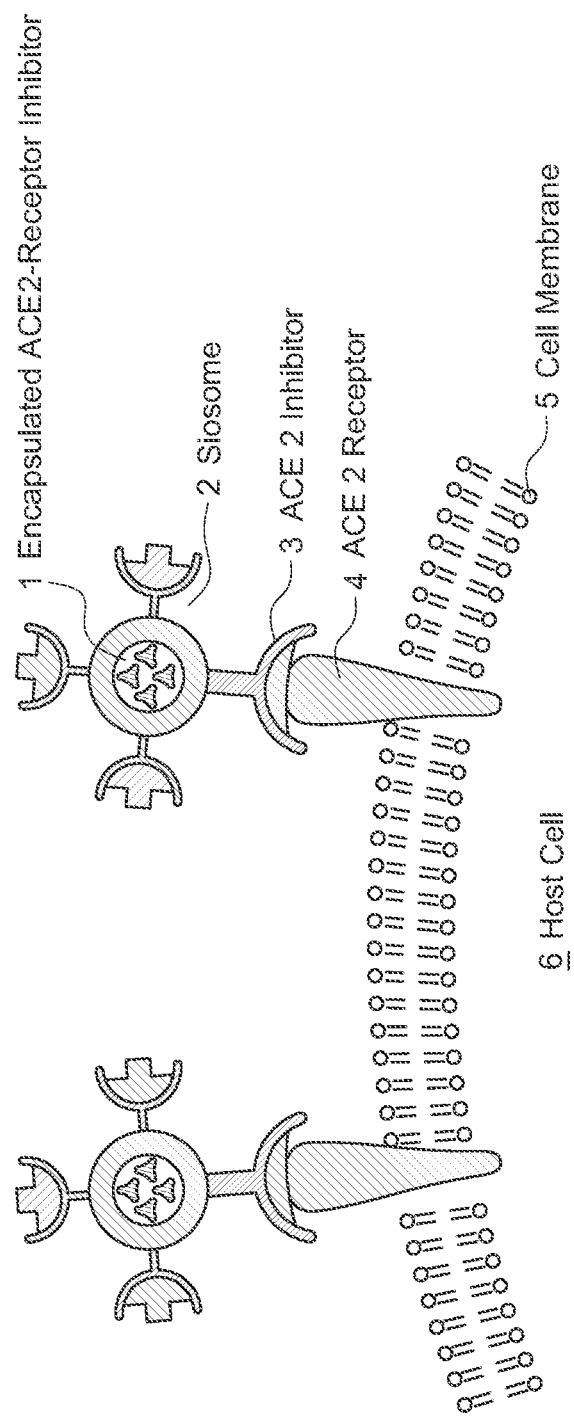
FIG. 1: Blocking the ACE 2 Receptors in the host cells using the ACE 2 inhibitor on the surface of the siosomes and the encapsulated ACE2 inhibitors in the siosomes after release.

The examples provided herein represent practical support for particular embodiments of the invention and are not intended to limit the scope of the invention. The examples are covering the following areas on the Multi-Target- and delivery Structure and effects of the siosomes and the compounds of the invention for the prophylaxis, prevention, attenuation, and/or therapy of said viral inflammations, Alzheimer's, neurodegenerative diseases, and neuromuscular degenerative diseases.

Example 1

Preparation of the Multi-Target and Delivery Siosomes for the Attenuation, Prevention and or Treatment of the Inflammations Caused by the SARS Co 2-V It is well recognized in the medical field that the most effective procedures for treating localized diseases and/or specific targeting of an organ, cell, receptors or cell compartments is to direct a pharmaceutical agent or active substance to the affected area, thereby avoiding undesirable toxic effects of systematic treatment.

Techniques and methods currently used in this invention to deliver active substances to specific target sites within the body involve the utilization of time-release delivery systems and the appropriate design of the multi-target and delivery system as mentioned below.

To reach the site of action, the API has to cross many biological barriers, such as other organs, cells and intracellular compartments, where it can be inactivated or express undesirable effects on organs and tissues that are not involved in the pathological process.

To achieve according to the invention the required objectives of the specific multi-target and delivery systems defined as:

1. Function of the Module 1-3

Module 1 to block and/or inhibit the ACE2 receptors in the host cells.

Module 2 to block and/or inhibit the spike protein of the SARS Co2 V virus.

Module 3 to block, interact, change and/or inhibit the internal compartments of the virion in the SARS Co2 V (e.g. RNA-protein nucleocapsid, membrane protein).

Module 3.1: "Inhibition of the SARS-CoV-2 virus" (Inhibition of viral RNA dependent RNA polymerase, blocking late stage of virus assembly) using in siosomes encapsulated, entrapped and/or conjugated polymerase inhibitors and siosomes transfection agents.

Module 3.2: "Inhibition of the SARS-CoV-2 virus" (Inhibition of viral RNA dependent RNA polymerase, blocking late stage of virus assembly) using polymerase inhibitors on the surface (outer layer) of the siosomes connected via cleavable and/or non-cleavable LINKERS.

2. Composition of the Module 1-3

According to the invention the method is characterized that the modules have the compositions:

Module 1: Siosomes with specific ACE2 receptor inhibitor and carbohydrate molecule on the surface of the siosomes and/or specific ACE2 inhibitor encapsulated, entrapped and/or conjugated in the siosomes.

Module 2: Siosomes with specific inhibitor of the spike protein and carbohydrate molecule on the surface of the siosomes.

Module 3.1: Siosomes encapsulated, entrapped and/or conjugated polymerase inhibitors and siosomes transfection agents.

Module 3.2 Siosomes with polymerase inhibitors on the surface (outer layer) of the siosomes connected via cleavable and/or noncleavable LINKERS.

Examples for structures of silanes and sugar silanes to provide a novel multi-target and delivery organosilicon siosomes nano system Example 1.1 (FIG. 1)

MODULE 1: Blocking the ACE2 Receptors e.g. in the human lung epithelial cells, heart cell, Kidney, GI using the siosomes nano carrier system. Each of the following 10 silanes/siosomes represent ONE module 1.

The 10 experiments in Example 1 with the ACE 2 inhibitor (captopril) will provide the following comparative data on the inhibition of the ACE2 receptor using the different compositions defined in the table. The objective will be to assess the composition which will achieve the best targeting and efficacy. (Figure)

1. Encapsulation of captopril in the siosomes
2. One molecule Captopril on the surface of the siosomes
3. Captopril on the surface and encapsulated in the siosomes
4. Two molecules of captopril on the surface of the siosomes
5. Influence of the sugar molecules on the surface of the siosomes
  One molecule sugar
  Two molecules of sugar
  Three molecules of sugar
6. Influence of amino acids on the surface of the siosomes
7. Influence of navigators on the surface
  One molecule of navigator (amino acid)
  Two molecules of navigator (amino acid)

TABLE 1

| | Silanes/Siosomes MODULE 1 | | |
|---|---|---|---|
| Silane/Siosomes No. MODULE 1 | Compounds on the surface/outer layer of the siosomes | Compounds in the mono/bilayer of the Siosomes | Compounds encapsulated, entrapped and/or conjugated in the siosomes |
| 1 | R1: Monosaccharide<br>R2: ACE2- Receptor Inhibitor | R3: Lipid chain<br>R4: Lipid chain | ACE2-Receptor Inhibitor |
| 2 | R1: Monosaccharide<br>R2: Monosaccharide | R3: Lipid chain<br>R4: Lipid chain | ACE2-Receptor-Inhibitor |
| 3 | R1: Monosaccharide<br>R2: ACE2 Receptor Inhibitor<br>R3: ACE2-Receptor Inhibitor | R4: Lipid | Monosccharide |
| 4 | R1: Monosaccharide<br>R2: Monosaccharide<br>R3: Monosaccharide | R4: Lipid | ACE2 Receptor Inhibitor |
| 5 | R1: Monosaccharide<br>R2: ACE2-Receptor Inhibitor<br>R3: Amino Acid (Leucin) | R4: Lipid | ACE2-Receptor Inhibitor |
| 6 | R1: Monosaccharide<br>R2: ACE2-Receptor Inhibitor<br>R3: Navigatiting molecule | R4: Lipid | ACE2-Receptor Inhibitor |

TABLE 1-continued

| | Silanes/Siosomes MODULE 1 | | |
|---|---|---|---|
| Silane/Siosomes No. MODULE 1 | Compounds on the surface/outer layer of the siosomes | Compounds in the mono/bilayer of the Siosomes | Compounds encapsulated, entrapped and/or conjugated in the siosomes |
| 7 | R1: Monosaccharide<br>R2: Monosaccharide<br>R3: Navigating molecule | R4: Lipid | ACE2-Receptor Inhibitor |
| 8 | R1: Monosaccharide<br>R2: Navigating molecule | R3: Lipid<br>R4: Lipid | ACE2-Receptor Inhibitor |
| 9 | R1: Monosaccharide<br>R2: Navigating molecule<br>R3: Navigating molecule | R4: Lipid | ACE2-Receptor Inhibitor |
| 10 | R1: Monosaccharide<br>R2: Amino Acid | R3: Lipid<br>R4: Lipid | ACE2-Receptor Inhibitor |

Example 1.2: (FIG. 2)

MODULE 2: Blocking the spike glycoprotein (S protein) on the virion surface with its subunits S1 and S2 of the SARS-CoV-2 Virus using the siosomes nanocarrier system. Each of the following 4 silanes/siosomes represent ONE module 2

Module 2 (FIG. 2)
1. Influence of monosaccharide (responsible for cell recognition and communication) on the surface of the siosomes on blocking of the spike glycoprotein (s protein): The objective will be to investigate the interaction of the monosaccharide with the spike glycoprotein and the blocking and inhibition of its targeting to the ACE2 receptors.
   One molecule sugar
   Two molecules sugar
   Three molecules sugar
2. Influence of amino acids and sugar on the surface of the siosomes. This to understand the impact of amino acids on the modification of the spike glycoprotein.
3. Influence of monosaccharide, dipeptides, polypeptides encapsulated in the siosomes.

Figure 3:
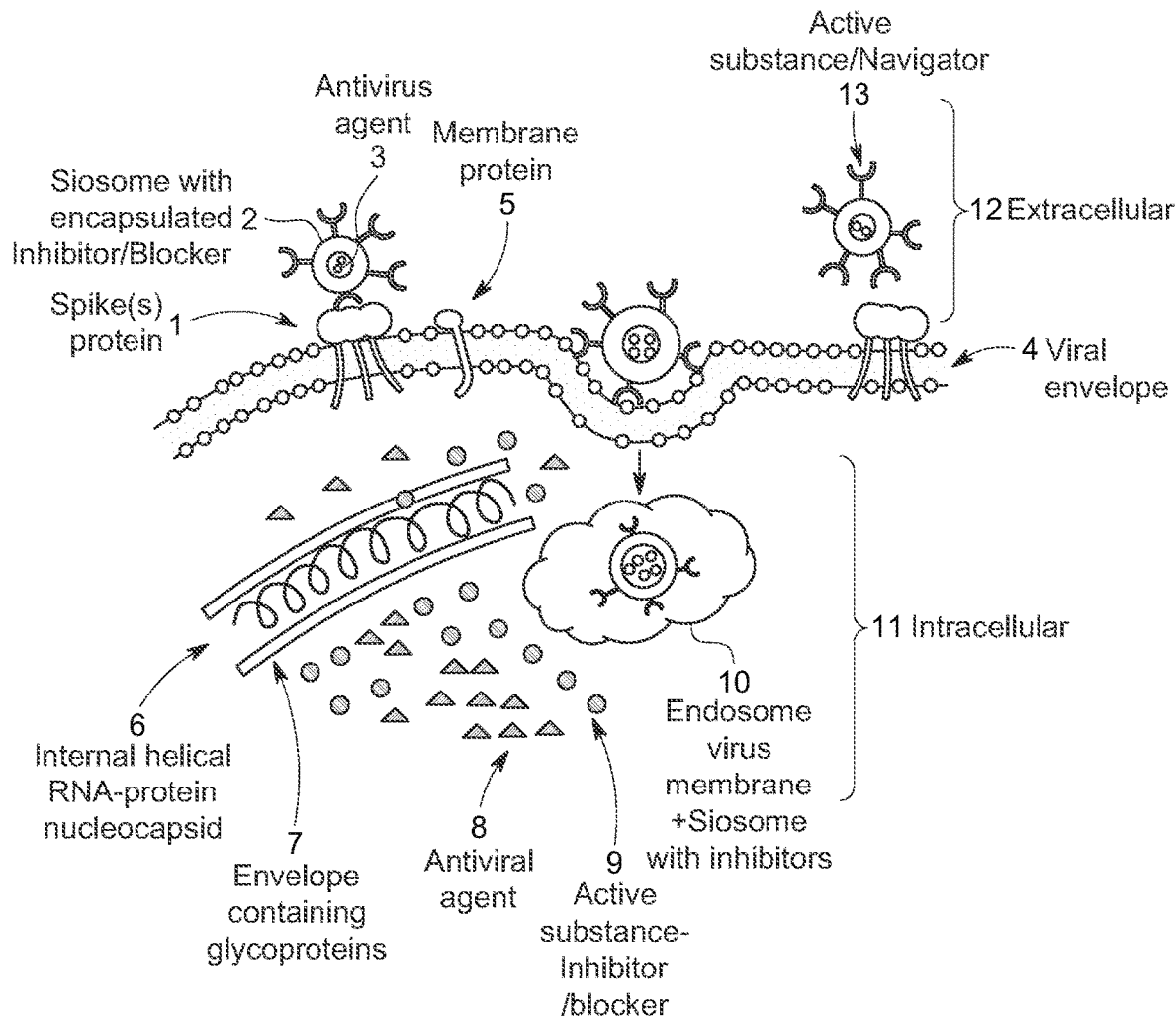
FIG. 3: (1) Blocking the spike (s) structural protein (1) with the effectors on the outer layer of the siosomes (13). (2) Inhibition of the virus (RNA) using the different siosomes with encapsulated antivirus agent.

Example 1.3.1 (FIG. 3)

MODULE 3.1: "Inhibition of the SARS-CoV-2 virus" (Inhibition of viral RNA dependent RNA polymerase, blocking late stage of virus assembly) using in siosomes encapsulated, entrapped and/or conjugated polymerase inhibitors. Each of the following 8 silanes/siosomes represent ONE module 3.1

Module 3.1 (FIG. 3)
1. Influence of monosaccharide on the surface of the siosomes on the transfection of the siosomes into the virus and the inhibition of the virion: The objective will be to investigate the impact of the monosaccharide on the transfection of the siosomes and the inhibition of the virion
   One molecule sugar
   Two molecules sugar
   Three molecules sugar
2. The influence of the different polymerase inhibitors which are encapsulated in the siosomes. The objective will be to investigate the influence of the sugar mol-

TABLE 2

| | Silanes/Siosomes MODULE 2 | | |
|---|---|---|---|
| Silane/Siosomes No. MODULE 2 | Compounds on the surface/outer layer of the siosomes | Compounds in the mono/bilayer of the Siosomes | Compounds encapsulated, entrapped and/or conjugated in the siosomes |
| 1. | R1: Monosaccharide<br>R2: Monosaccharide | R3: Lipid<br>R4: Lipid | Monosaccharide |
| 2. | R1: Monosaccharide<br>R2: Monosaccharide | R3: Lipid<br>R4: Lipid | Polysaccharide |
| 3. | R1: Monosaccharide<br>R2: Monosaccharide<br>R3: Monosaccharide | R4: Lipid | Monosaccharide |
| 4. | R1: Monosaccharide<br>R2: Monosaccharide<br>R3: Amino Acid | R4: Lipid | Dipeptide/polypeptide |
| 5. | R1: Monosacaride<br>R2: Monosaccharide | R3: Peptid<br>R4: Lipid | Dipeptide/polypeptide | ecules on the targeting and efficacy of the polymerase inhibitors.
Camostat
R Remdisivir
Kaleta
R Avigan
MRNA
Sodium meta arsenite

TABLE 3.1

| | Silanes/Siosomes MODULE 3.1 | | |
|---|---|---|---|
| Silane/Siosomes No. MODULE 3.1 | Compounds on the surface/outer layer of the siosomes | Compounds in the mono/bilayer of the Siosomes | Compounds encapsulated, entrapped and/or conjugated in the siosomes |
| 1 | R1: Monosaccharide<br>R2: Monosaccharide | R3: Lipid<br>R4: Lipid | Polymerase inhibitor "Camostat mesylate" |
| 2 | R1: Monosaccharide<br>R2: Monosaccharid<br>R3: Monosaccharide | R4: Lipid | Polymerase Inhibitor "Camostat Mesylate" |
| 3 | R1: Monosaccharide<br>R2: Monosaccharide linked with PEG | R3: Lipid<br>R4: Lipid | m-RNA |
| 4 | R1: Monosaccharide<br>R2: Monosaccharide | R3: Lipid<br>R4: Lipid | Polymerase inhibitor: Remdisivir |
| 5 | R1: Monosaccharide<br>R2: Monosaccharid<br>R3: Monosaccharide | R4: Lipid | Polymerase inhibitor: Remdisivir |
| 6 | R1: Monosaccharide<br>R2: Monosaccharide | R3: Lipid<br>R4: Lipid | sodium metaarsenite - tolemerase inhibitor |
| 7 | R1: Monosaccharide<br>R2: Monosaccharide | R3: Lipid<br>R4: Lipid | Protease inhibitor: Kaletra |
| 8 | R1: Monosaccharide<br>R2: Monosaccharide | R3: Lipid<br>R4: Lipid | AVIGAN (Favipiravirand metabolite Favipiravir-ribofuranosyl-5'-triphosphate(Favipiravir-RTP): Inhibitor of viral RNA dependent RNA Polymerase |

Example 1.3.2 (FIG. 3)

MODULE 3.2 "Inhibition of the SARS-CoV-2 virus" (Inhibition of viral RNA dependent RNA polymerase, blocking late stage of virus assembly) using polymerase inhibitors on the surface (outer layer) of the siosomes connected via cleavable and/or noncleavable LINKERS and cationic siosomes as "transfection agents". Each of the following 4 silanes/siosomes represent ONE module 3.2 The objective will be to investigate the following;
1. Influence of the polymerase inhibitor on the surface (outer layer) of the siosomes and cationic siosomes as "transfection agents" on the inhibition of the virion.
2. The influence of the polymerase inhibitors
Camostat mesylate
Remdisivir

TABLE 3.2

| | Silanes/Siosomes MODULE 3.2 | | |
|---|---|---|---|
| Silane/Siosomes No. MODUL 3.2 | Compounds on the surface/outer layer of the siosomes Linker with the Siosomes | Compounds in the mono/bilayer of the Siosomes | Compounds encapsulated, entrapped and/or conjugated in the siosomes. |
| 1. | R1: Monosaccharide<br>R2: Camostat-Linker-Siosomes | R3: Lipid<br>R4: lipid | Polymerase inhibitor "Camostat mesylate |
| 2. | R1: Monosaccharide<br>R2: Remdisivir - Linker-Siosomes | R3: Lipid<br>R4: Lipid | Polymerase inhibitor: Remdisivir |
| 3. | R1: Monosaccharide<br>R2: Kaletra -Linker-Siosomes | R3: Lipid<br>R4: Lipid | Protease inhibitor: Kaletra |
| 4. | R1: Monosaccharide<br>R2: Monosaccharide | R3: Lipid<br>R4: Avigan-Linker-Siosomes | AVIGAN |

Example 2

Determination of the cytotoxicity and antiviral Activity of 43 selected silanes and sugar silane/siosomes with different chemical groups and structures I. Outlines (1) Screening of the 43 silanes and sugar silanes for antiviral activity against model viruses belonging to taxonomic groups including causative agents of infections in which applications of chemotherapy is strongly indicated.
   a) Enterovirus B (or C) (Family Picornaviridae)
   b) Bovine Viral Diarrhea virus (a surrogate hepatitis C virus) (Family Flaviviridae)
   c) Influenza virus A (Family Orthomyxoviridae)
   d) Respiratory syncytial virus (Family Paramyxoviridae)
   e) Human adenovirus 2 (or 5) (Family Adenoviridae)
   f) Herpes simplex virus type 1, and
   g) Human cytomegalovirus (Family Herpesviridae)
   h) Vaccinia virus (Family Poxviridae)

(2) The antiviral screening was performed in-vitro in cell cultures. The CPE inhibition test in monolayer cell cultures (in micro plates); photometrical (optical density) measurement of neutral red uptake was carried out. In parallel, cytotoxicity has been determined.
   Compounds manifesting antiviral effects has been included in some additional tests for in-vitro antiviral activity illustration.

Determination of Cytotoxicity

The neutral red uptake assay based on the initial protocol described by Borenfreund and Puerner (1984) was used. Monolayer cells in 96-well plates are inoculated with 0.1 ml of the tested solution in several serial dilutions performed in a maintenance medium. Cells inoculated with 0.1 ml maintenance medium (no compound in the medium), serve as a control. Each tested dilution is inoculated in 6 wells of the cell culture plate. Then, the cells were incubated at 37° C. in a humidified atmosphere with 5% $CO_2$ and the cell vitality at the 48', $72^{nd}$ or $96^{th}$ hour was estimated (following light microscopy observation) using ELISA reader at $OD_{540\,nm}$. The 50% cytotoxic concentration ($CC_{50}$) is calculated in comparison to the cell control by applying the regression analysis with the help of Origin 6.1 computer program.

Determination of Antiviral Activity

The cytopathic effect (CPE) inhibition test is used for measuring the antiviral effect. Monolayer cells in 96-well plates are inoculated with 0.1 ml virus suspension containing 100 $CCID_{50}$. After an hour for virus adsorption (two hours in the case of HRSV-A2) in a humidified atmosphere at 37° C. and 5% $CO_2$, excessive virus is discarded and cells are inoculated with 0.2 mL of maintenance medium containing serial 0.5 lg dilutions of the tested preparation. Mock-infected cells are left for cell and toxicity controls. The virus CPE is scored daily by inverted light microscope (Olympus CK40, Japan) at 125× and 400× magnification on a 0-4 basis (4 representing total cell destruction) till the appearance of its maximum in the virus control wells (with no compound in the maintenance medium)—the 48' hour p.i. for PV1, $72^{nd}$ hour for HRSV-A2 and the 4th day ($96^{th}$ hour) p.i. for HAdV-2. When maximum CPE in the virus control wells is reached, cells are processed according to the neutral red procedure described above. The percent of virus CPE protection is calculated by the following formula [Pannecouque et al., 2008]:

$$\frac{meanOD_{Test} - meanOD_{VC}}{meanOD_{TC} - meanOD_{VC}} \times 100$$

$(OD_{Test}-OD_{VC})/(OD_{TC}-OD_{VC})\times100(\%)$, where $OD_{Test}$ is the mean optical density (OD) of the test sample, $OD_{VC}$—the absorbance of the virus-infected control (no compound in the maintenance medium), and $OD_{TC}$—the OD of the mock-infected control (toxicity control).

The 50% virus inhibitory concentration ($IC_{50}$) is determined by applying the regression analysis with the help of Origin 6.1 computer program and it is expressed as the concentration that achieves 50% protection of virus-infected cells.

The selectivity index (SI) is evaluated as the ratio between $CC_{50}$ and $IC_{50}$ ($SI=CC_{50}/IC_{50}$).

Each of the tests described above was done in triplicate to quadruplicate, with four cell culture wells per test sample.

Antiviral Activity

The screening carried out for antiviral activity in vitro (in cell culture experiments) of 43 Silanes and sugar silanes according to General Formel 1 embraced eight viruses belonging to taxonomic entities (families) including causative agents of infections to which chemotherapy is indicated.

The results obtained demonstrated a marked activity of Silane No. 27 (SIL27) only against human cytomegalovirus: SI=30.9.

Silane No. 20 (SIL 20) showed a marked activity as well toward the cytomegalovirus: at a low m.o.i. (3.2 CCID50 per microplate well)

Close to borderline effect against this virus cytomegalovirus was found by Silanes SIL2, SIL7, SIL15, SIL 19 and SIL 34 and Silanes SIL 2, SIL3 and SIL 25 showed marked activity toward influenza virus A(H3N2).

Silane SIL 9 showed marked activity versus vaccinia virus.

No one of the Silanes manifested activity towards PV1, BVDV, RSV, HuAdV2 and HSV type 1.

Cytotoxicity Activity

As concerns the cytotoxicity it was established a strong variation towards different cell Cultures used.

Higher cytotoxicity values (CC50<20 µM) were recorded as follows:
Silanes 1, 2, 5, 21, 22, 23, 24, 26 and 36 towards HEp-2 cells,
Silanes 1, 2, 3, 5 and 25—toward CT cells,
Silanes 2, 3 and 26 toward MDCK cells,
Silanes 1, 2 and 3 toward MDBK cells,
Silanes 4, 7, 22, 23, 24 and 32 toward MRC-5 cells
Silanes 5, 21 and 36 vs Vero cells.

Summarizing the cytotoxicity data it could indicate several compounds possessing wider toxicity, on more than one cell culture:
Silane 1—on HEp-2 cells, CT cells and MDBK cells
Silane 2—on HEp-2, CT and MDCK cells
Silane 5—on HEp-2, CT, MDBK and Vero cells
Silanes 22, 23 and 24—on HEp-2 and MRC-5 cells
Silane 26—on HEp-2 and MDCK cells
Silane 36—on HEp-2 and Vero cells.
Silane 21 manifested a marked cytotoxicity only on HEp-2 cells.

Comparing the cytotoxicity susceptibility of the different cell cultures species it could marked the higher susceptibility of the HEp-2 cells.

Evidently, the realization of quantitative structure-activity relationship (QSAR) of the silanes included in this study would contribute for the further planned synthesis of active antiviral compounds, especially directed against HCMV.

Discussion

Antiviral Activities

Surprisingly and unexpected 10 silanes and sugar silanes have shown antiviral activities with the following investigated enveloped viruses (Table 4):

Human Cytomegalvirus (HCMV) consists of an outer lipid bilayer envelope, composed of various viral glycoproteins.

Influenza virus A (virion as the infectious particle) is roughly spherical. It is an enveloped virus—that, the outer layer of the viron is a lipid membrane.

Vaccinia virus (VACV or VV) is a large, complex, enveloped virus.

These viruses are enveloped viruses as the SARS viruses and the SARS Co-2V.

The investigated silanes and sugar silanes have different chemical structures such as the following differences:

- Different residues on the surface of the siosomes (sugar molecules, Phenyl, methyl . . . )
- Number and length of the lipid chain(s)
- Electrical charges of the molecule
- Physicochemical properties (solubility, stability, chemical reactions)
- The 7 Silanes 2, 3, 7, 9, 15, 19, 20 belong to the "Sugar Silanes" with sugar molecules on the surface of the siosomes nano particles.
- The 3 Silanes 25, 27, 34 belong to the Silanes and have other molecules than sugar on the surface of the siosomes.

With reference to the unexpected antiviral results in the invention, it be concluded:

- The sugar silanes and silanes are suitable as multi-target and delivery systems
- The sugar molecules on the surface of the siosomes are very relevant for the interaction with the receptors in the host cell, and/or they block it.
- The sugar and other residues on the surface of the siosomes are relevant for the recognition, communication, interaction, blocking and/or inhibition of the virus.
- The siosomes could penetrate and transfect the envelope of the virus and inhibit the virion activities.
- The siosomes are appropriate for the encapsulation, entrapment, and/or conjugation of the different active substance including, but not limited to antiviral agents, antibacterial, transfection agents, peptides and oxidants.
- The siosomes are appropriate to be as inhibitors to the viruses via fusion with the Virus.
- The silanes and sugar Silanes are appropriate according to the invention to be linked to antibodies, and active agents.
- The use of antiviral silanes and sugar silanes could have additive antiviral activities when it is encapsulated, entrapped or conjugated with antiviral agents.

Cytotoxicity Activities

Surprisingly and unexpected that a number of the investigated silanes and sugar silanes with different molecular structure have shown cytotoxicity.

As a total 14 Silanes and Sugar Silanes have shown cytotoxicity activities. They are as follows:

- The 6 silanes 1, 2, 3, 4, 5, 7, belong to the "Sugar Silanes" with sugar molecules on the surface of the siosomes nano particles.
- The 8 Silanes 21, 22, 23, 24, 25, 26, 32, 36 belong to the silanes and have other molecules than sugar on the surface of the siosomes.
- It is also unexpected that only the following three (3) sugar silanes 2, 3, 7 and one (1) non-sugar silane No. 25 have shown in addition to the antiviral activities cytoxicity.

It is surprisingly unexpected that 23 Silanes and Sugar Silanes of the 43 investigated compounds approximately 53% are inert. The silanes and Sugar silanes and their derivatives according to the invention provide a great diversity of multi-target and delivery carrier for the encapsulation, entrapment, conjugation with active substances as for the attenuation, prevention and/or treatment of viral infections and diseases caused by SARS viruses such as SARS Co 2-V.

TABLE 4

Silanes and sugar silanes with anti-virus activities

| No. | Structure and Name | Molecular Formula | MW (Da) |
|---|---|---|---|
| Sil 2 | 2-(Dimethyldecylsilyl)ethyl-b-D-glucopyranosid | C20H42O6Si | 406.64 |
| Sil 3 | 2-(Dimethyldodecylsilyl)ethyl-b-D-glucopyransosid | C22H46O6Si | 434.69 |

TABLE 4-continued

Silanes and sugar silanes with anti-virus activities

| No. | Structure and Name | Molecular Formula | MW (Da) |
|---|---|---|---|
| Sil 7 | 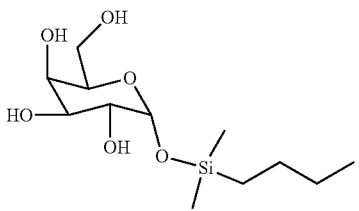<br>Butyldimethylsilyl-a-D-galactopyranosid | C12H26O6Si | 294.42 |
| Sil 9 | 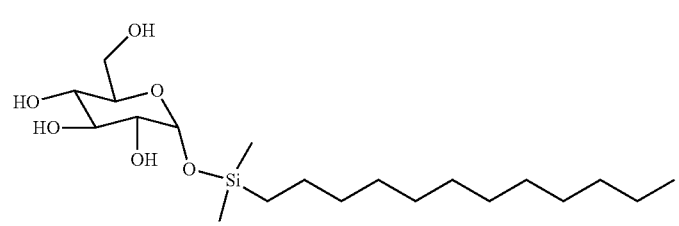<br>Dodecyldimethylsilyl-a-D-glucopyranosid | C20H42O6Si | 406.64 |
| Sil 15 | 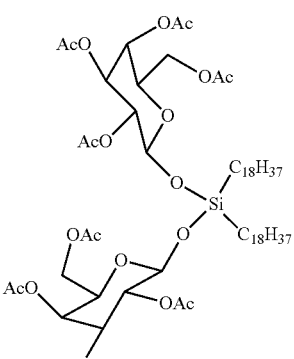<br>1-O-Dioctadecylsilyl-di(2,3,4,6-O-tetraacetyl-b-D-galactopyranosid) | C64H112O20Si | 1229.68 |
| Sil 19 | 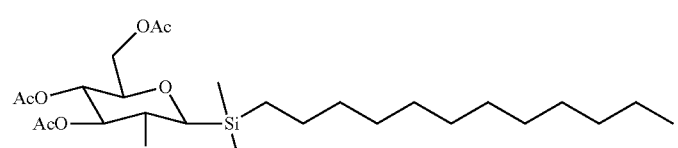<br>1-O-Dimethyl(dodecyl)silyl-(2,3,4,6-O-tetraacetyl-b-D-glucopyranosid) | C28H50O10Si | 574.79 |
| Sil 20 | 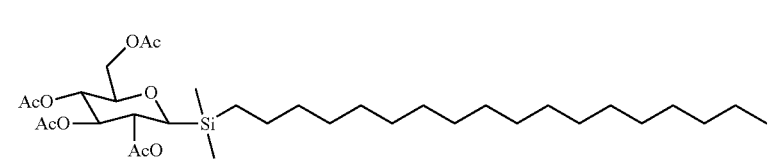<br>1-O-Dimethyl(octadecyl)silyl-(2,3,4,6-O-tetraacetyl-b-D-glucopyranosid) | C34H62O10Si | 658.95 |

TABLE 4-continued

Silanes and sugar silanes with anti-virus activities

| No. | Structure and Name | Molecular Formula | MW (Da) |
|---|---|---|---|
| Sil 25 | Di(dodecanoyloxy)diphenylsilan | C36H56O4Si | 580.93 |
| Sil 27 | Di(hexadecanoyloxy)diphenylsilan | C44H72O4Si | 693.15 |
| Sil 34 | Di(undecanoyloxy)dimethylsilan | C24H48O4Si | 428.73 |

TABLE 5

Cytotoxicity and antiviral activity of silanes on the replication of influenza A(H3N2) Aichi virus in MDCK cells (as an example)

| Compound | $CC_{50}$ (μM) | $IC_{50}$ (μM) | SI |
|---|---|---|---|
| Sil 1 | 30.0 | — | — |
| Sil 2 | 18.0 | 7.38 | 2.43 |
| Sil 3 | 19.2 | 6.6 | 2.9 |
| Sil 5 | 32.0 | — | — |
| Sil 7 | 444.2 | — | — |
| Sil 8 | 23.5 | — | — |
| Sil 9 | 444.2 | — | — |
| Sil 10 | 156.0 | — | — |
| Sil 11 | 444.2 | — | — |
| Sil 19 | 65.5 | — | — |
| Sil 20 | 2533.0 | — | — |
| Sil 21 | 21.0 | — | — |
| Sil 22 | 42.9 | — | — |
| Sil 23 | 93.2 | — | — |
| Sil 24 | 32.0 | — | — |
| Sil 25 | 55.9 | 9.6 | 5.82 |
| Sil 26 | 19.0 | — | — |
| Sil 27 | 317.0 | — | — |
| Sil 31 | 52.1 | — | — |
| Sil 32 | 45.2 | — | — |
| Sil 33 | 155.0 | — | — |
| Sil 34 | 2533.0 | — | — |
| Sil 42 | 398.0 | — | — |
| Sil 43 | 137.0 | — | — |
| Sil 44 | 537.0 | — | — |
| Sil 45 | 560.0 | — | — |
| Rimantadine | 94.0 | 0.03 | 3133.0 |

Effect Against Influenza Virus a (H3N2)

Figure 10:
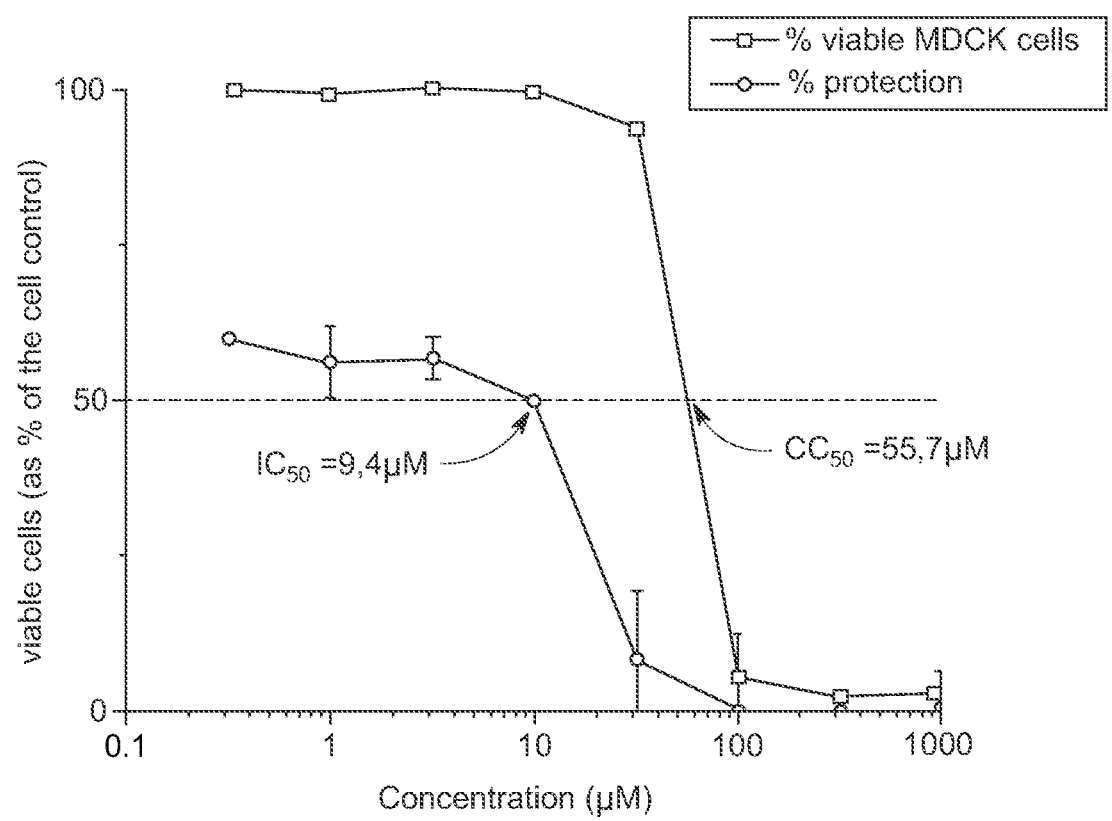
FIG. 10: Effect against influenza virus A (H3N2)—Example for the antiviral activity of SIL 25.
Figure 11:
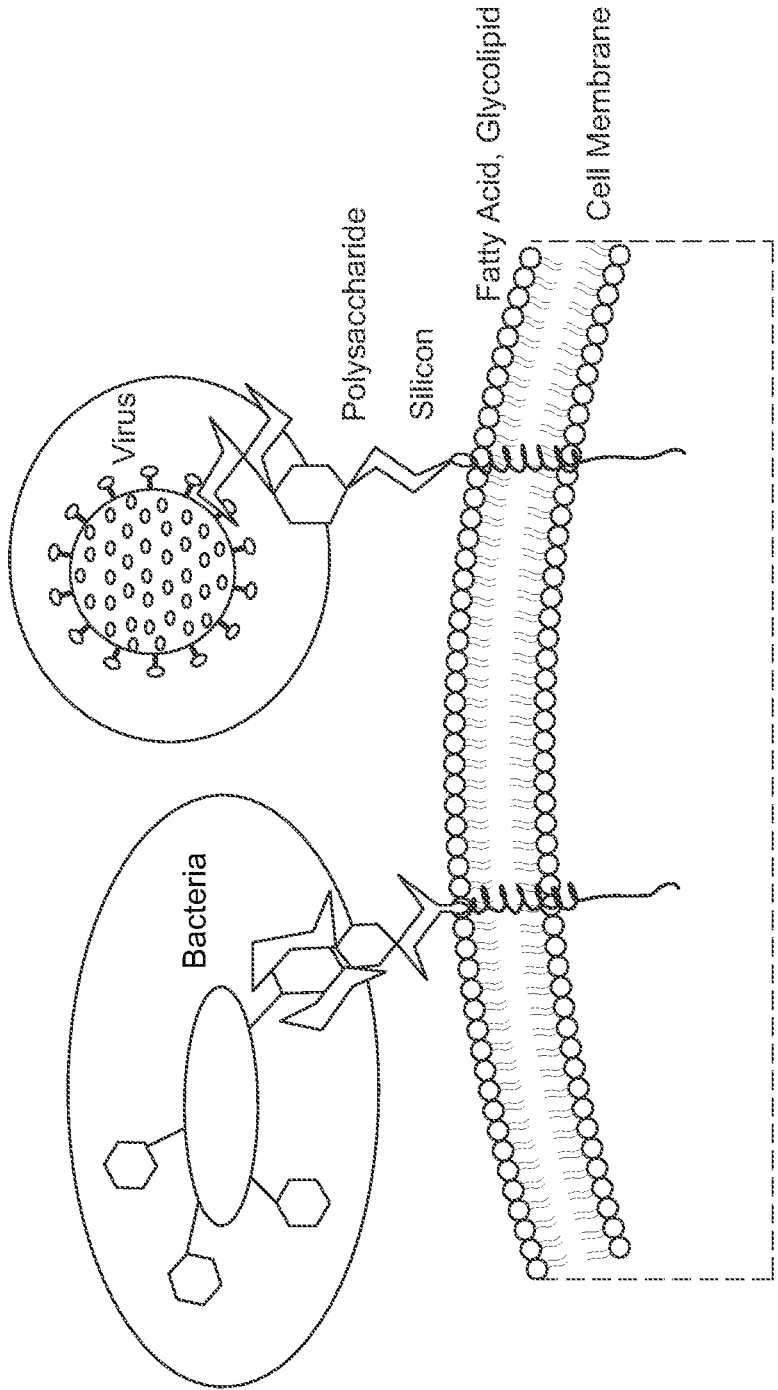
FIG. 11: Importance of sugar residues in the sugar Silanes and Siosomes for targeted binding against viruses, bacteria and cancer cells (Salama).

FIG. 10: Cytotoxicity and antiviral activity of silanes on the replication of influenza virus A/Aichi/2/68 (H3N2) in MDCK cells—SIL 25

Example: Sugar Silane—SIL 25

Example 3

Tissue Distribution Results for Study Number IPSS E010 after Repeated (Seven Continuous Days 1 mg Each Day) Administration of Cis-Oxoplatin (Oral and Intravenous) and Cis-Oxoplatin Siosome Complex (Intravenous)—No Non Treatment Period (Rats Sacrificed 24 Hrs after Last Administration)

Objectives

To investigate the influence of the encapsulation of cis-oxoplatin as a reference compound from the active substances according to the invention on the tissue distribution in comparison to the un-encapsulated cis-oxoplatin.

The molar adjustment had been taken into consideration for the determination of the distributed cis-oxoplatin in the different tissues.

The cis-oxoplatin siosome complex has the highest concentration in blood, kidney and adipose tissue.

Standard cis-oxoplatin administered intravenously has the highest platinum concentration in the stomach and the liver.

The standard cis-oxoplatin oral has the highest accumulation of platinum in the spleen and lungs.

The highest tissue accumulation for all treatment groups was found in the kidneys, though the blood had the highest concentrations.

TABLE 6

Percentage of Total Platinum in Each Tissue as a Percentage of Administered Total Platinum

| Tissue | Standard Cis-Oxoplatin Oral | Standard Cis-Oxoplatin i.v. | Cis-Oxoplatin Siosome Complex i.v. |
|---|---|---|---|
| Stomach | 0.011% | 0.022% | 0.026% |
| Liver | 0.201% | 1.190% | 1.032% |
| Lung | 0.048% | 0.039% | 0.054% |
| Kidney | 0.170% | 0.577% | 0.789% |
| Spleen | 0.035% | 0.045% | 0.054% |
| Adipose Tissue | 0.005% | 0.035% | 0.075% |
| Blood | 0.306% | 0.658% | 0.835% |
| Total | 0.776% | 2.566% | 2.865% |

Surprisingly and unexpected that the tissue with the highest actual content of total platinum by mass was the liver for all treatment groups. The total measured mass as a percentage of the platinum initially administered within the tissues and blood collected of total platinum was 0.776% for the standard cis-oxoplatin administered orally, 2.566% for the standard cis-oxoplatin administered intravenously and 2.865% for the cis-oxoplatin encapsulated in siosomes administered intravenously. These values are percentage of total platinum found in the six organs tested compared to the amount of total Discussion of the Results In this example for the tissue Distribution study in rats. Cis-oxoplatin as ant-viral agent encapsulated in the siosomes and the animals have been administered the two preparations intravenously.

Cis-oxoplatin has been encapsulated in the siosomes and Free cis-oxoplatin as (un-encapsulated). Both products were administered intravenously to the animals.

The unexpected and surprisingly results have shown the following: The concentration and content of cis-oxoplatin in the following organs and blood for the encapsulated cis oxoplatin formulation were higher compared to the un-encapsulated cis-oxoplatin:

Lung: 38%

Kidneys: 36%

Spleen: 20%

Blood: 27%

Blood and the organs lungs, kidneys and spleen and especially the lungs are the most important organs along with the heart and liver for the infection activities and organ dysfunction caused by the virus and particularly SARS Co2V and the other SARS viruses.

It is therefore a great advantage of the encapsulated and/or entrapped antiviral agents of the active substances. This will increase the accumulation of the antivirus agent in these relevant organs and tissues which will be infected by the virus. This will improve in addition the bioavailabilty of the antiviral drug in the blood and organs and increase the efficacy.

Furthermore In there is the possibility to design and customize further multi-target and delivery siosomes in order to increase these positive antiviral effects.

Example 4

Synthesis of a Sugar Silane for the Conjugation to Monoclonal Antibodies and Protein for the Preparation of the Siosomes-Monoclonal Antibody Conjugate Description Synthesis of a sugar silane for use for conjugation to monoclonal antibodies and proteins for the preparation of Siosomes. The sugar silane will be the SIL 17 (with 2 sugar molecules replaced with:

(1) Tri-peptide QPG (Si-QPG)

(2) Non-cleavable linker contains a spacer and a maleimide functional group.

The spacer could be with short chain. This means no need for PEG to avoid steric hindrance for the reaction of the maleimide with the mAB.

Mesylate-Azide Route

This approach is based on partial conversion of a di-mesylate in a mesylate azide intermediate. A Grignard addition of dodecyl-magnesium chloride to dodecyl-trichlorosilane followed by a double Grignard with vinyl magnesium chloride to give intermediate 3. Hydroboration and treatment with MsCl should give dimesylate 5. Treatment with a single equivalent of azide will hopefully result in mixture containing compound 6 as isolatable component. The yield is expected to be low because a literature reference used a similar approach and isolated the mono-mesylate in 18% yield. The mesylate may be used to alkylate the tripeptide. Subsequent reduction of the azide will give amine 9 that can be coupled to active ester 10.

Scheme 1
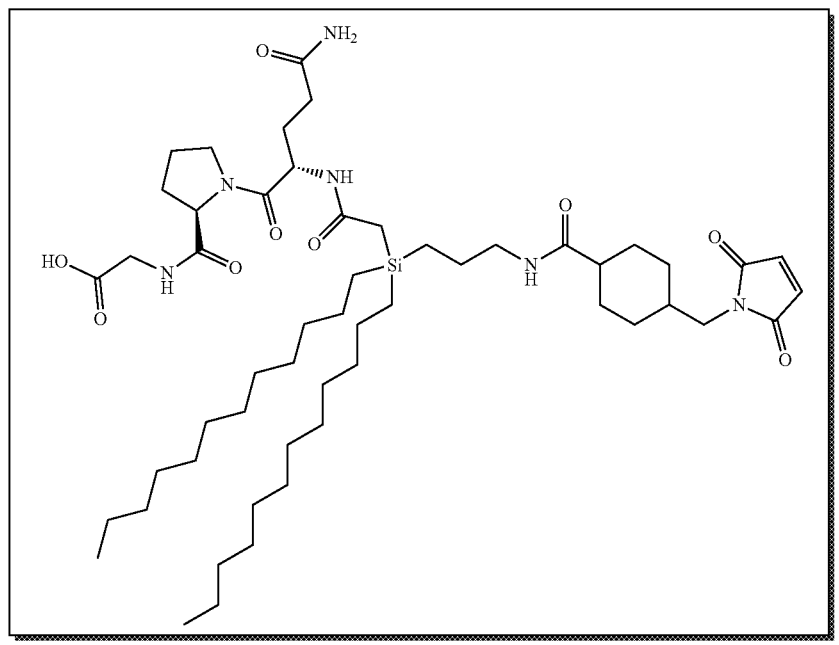
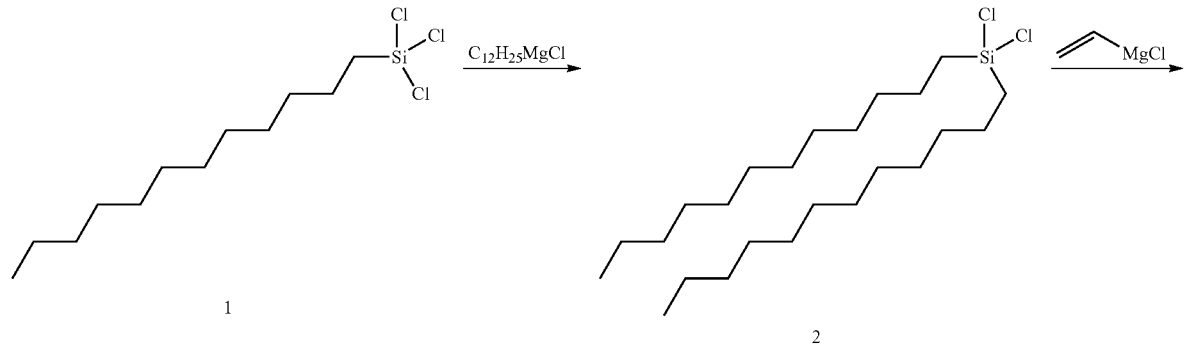
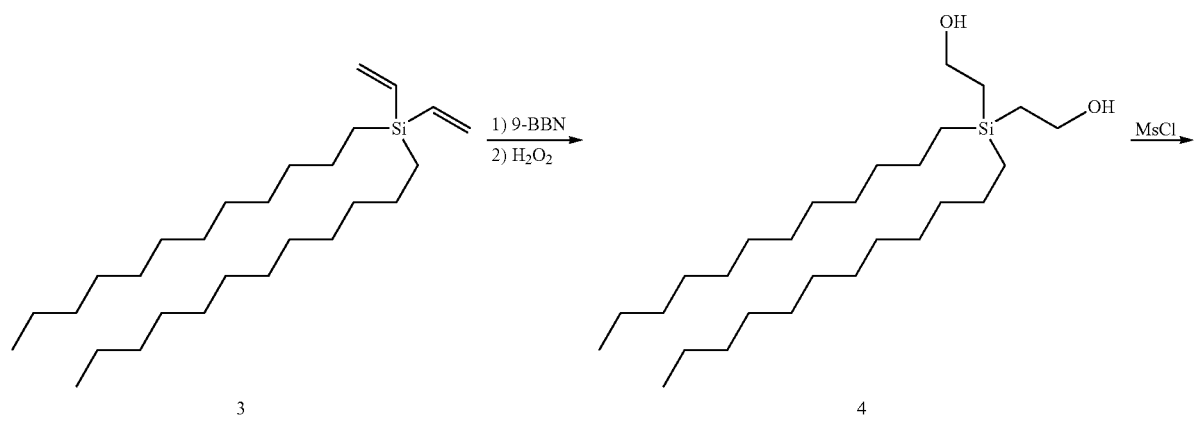

-continued
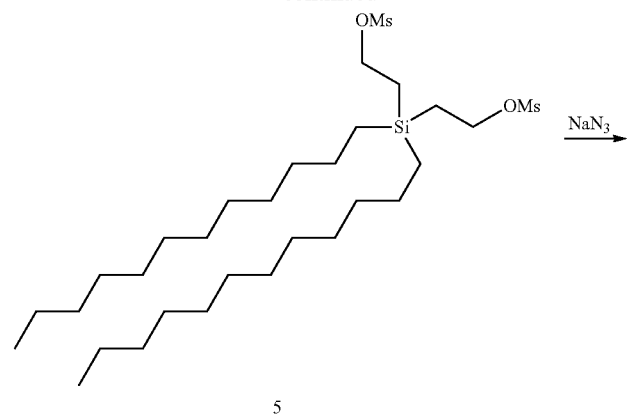
5
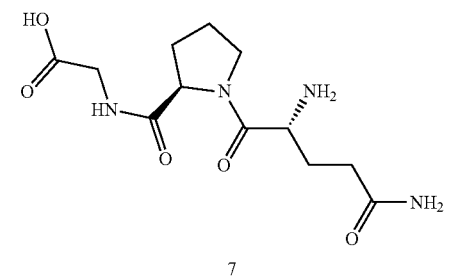
7
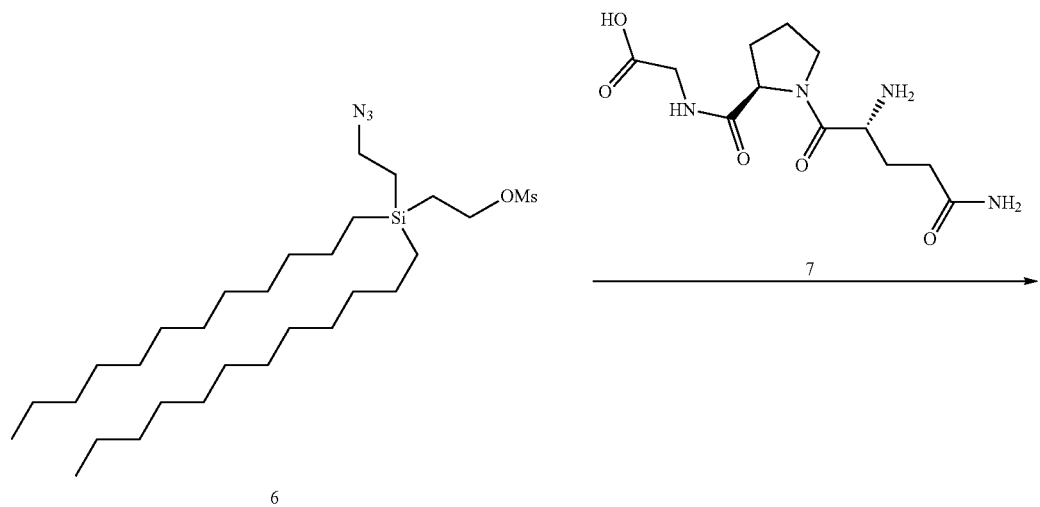
6
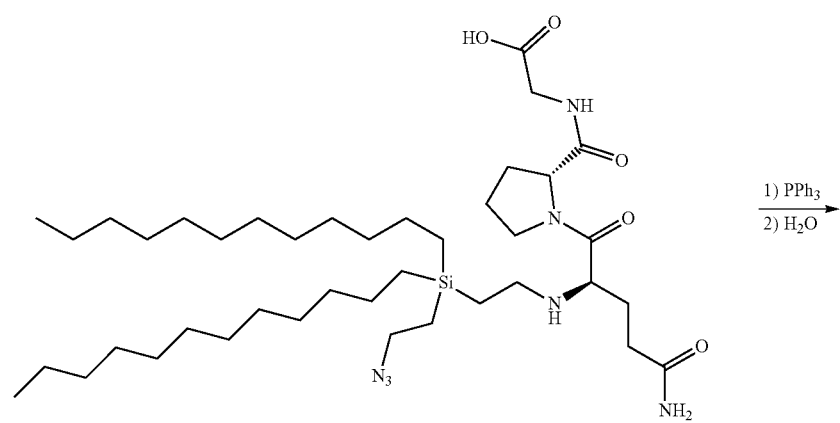
8

This is one of the many possibilities that the silanes, sugar silanes and their derivatives offer to conjugate with the monoclonal antibodies, and proteins to produce siosomes with the monoclonal antibodies on the surface SABC (Siosomes Antibody Conjugate) (FIG. 12).

In addition, as further possibilities are: the production of the following siosomes conjugates:
Siosomes-Genetic materials conjugate SGMC (FIG. 13)
Siosome Antivirus Drugs Conjugates SADC (FIG. 13)
Siosomes-Corticosteroids Conjugates SCC (Fig)
Siosomes-Active substances-conjugates such as polymers, etc.

It is unexpected that the manufacture of Siosome Conjugates with pharmaceuticals such as anti-cancer, antivirus, antibiotics and corticosteroids will have many advantages compared to the process known in the prior art as "ADC" Antibody Drug Conjugate. A number of the advantages of the siosomes are:

Easy chemistry—chemical reactions between the silane molecules or sugar silanes and the antivirus, antibiotics, non-cytotoxic compounds instead of reaction/conjugation of a drug molecule with a 3D biological molecule like a monoclonal antibody.

The isolation and characterization of the siosome conjugates is not as complex as with biological molecules.

Scale up GMP production of the siosomes conjugate is easier because it is considered as pharmaceutical drug product.

The siosomes conjugates with pharmaceuticals as drug molecules are much more stable than conjugates with biological materials due to risk of e.g. aggregation, degradation, etc.

Development and production times for siosomes conjugates are shorter and the costs are cheaper.

The siosomes conjugates with drugs are multi-target and delivery systems with better targeting than the monoclonal antibody Drug conjugates This is because of the navigating and targeting molecules on the surface of the siosome. In addition the monoclonal antibodies are designed to target only one antigen or receptor.

The documentations required for the marketing authorization of the siosomes conjugates as pharmaceuticals is less comprehensive than for the monoclonal antibody drug conjugates. This will shorten the development time and reduce the costs.

Example 5

1. Preparation of a Siosome Multi-Target and Delivery of Sugar Organosilicon Compound (Sugar Silane) with Captopril ((S)-1-(3-Mercapto-2-Methyl-1-Oxoropyl)-L-Proline Als ACE2 Inhibitor (Siosomes No. 2—Module 1).

Captopril Encapsulated in Siosomes Prepared from Sugar Silane SIL17

A dispersion of 10 µmol of Didodecylsilyl-di(2,3,4,6-O-tetraacetyl-β-D-glucopyranosid) as the representative of amino sugar organosilicon compound, 0.01M Tris/HCl, pH 7.4 and an aqueous solution of Captopril (10 µmol, volume 3 ml) was prepared by mixing with a high pressure homogeniser. The homogenisation time may vary. The mixture was then incubated at 37° C. for 60-90 minutes and sterile filtrated and lyophilised at the temperature of −70° C. The lyophilised-amino sugar organosilicon complex was reconstituted by hydration in sterile (deionized) water and the carrier system solution was used for in-vitro investigations.

After reconstitution by rehydration, the said carrier system surprisingly retains in solution more than 95% of the captopril. The yield of the preparation process resulted from 3 independent experiments, and was 80-90% of the starting concentrations. Stability tests performed at 0, 4, 8, 12 and 48 hours at 4° C., 25° C. and 37° C. have shown that the carrier system complex of organosilicon captopril is surprisingly stable and retains its activity.

Figure 6:
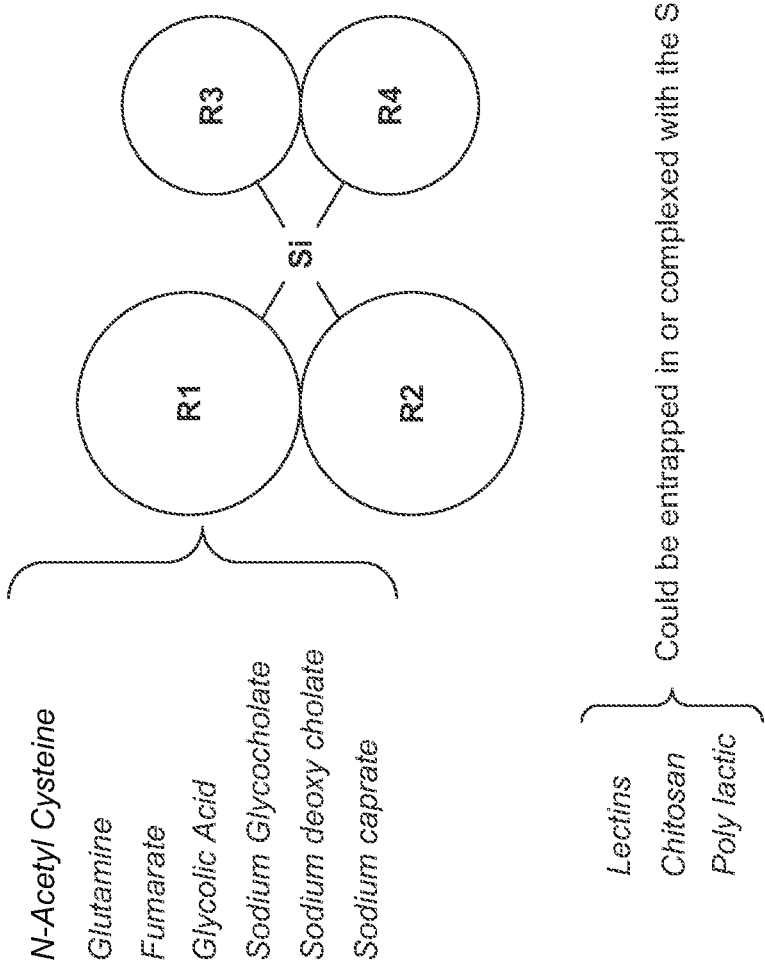
FIG. 6: Specific targeting of the GI using the Siosomes as multi-target and delivery system.
Figure 7:
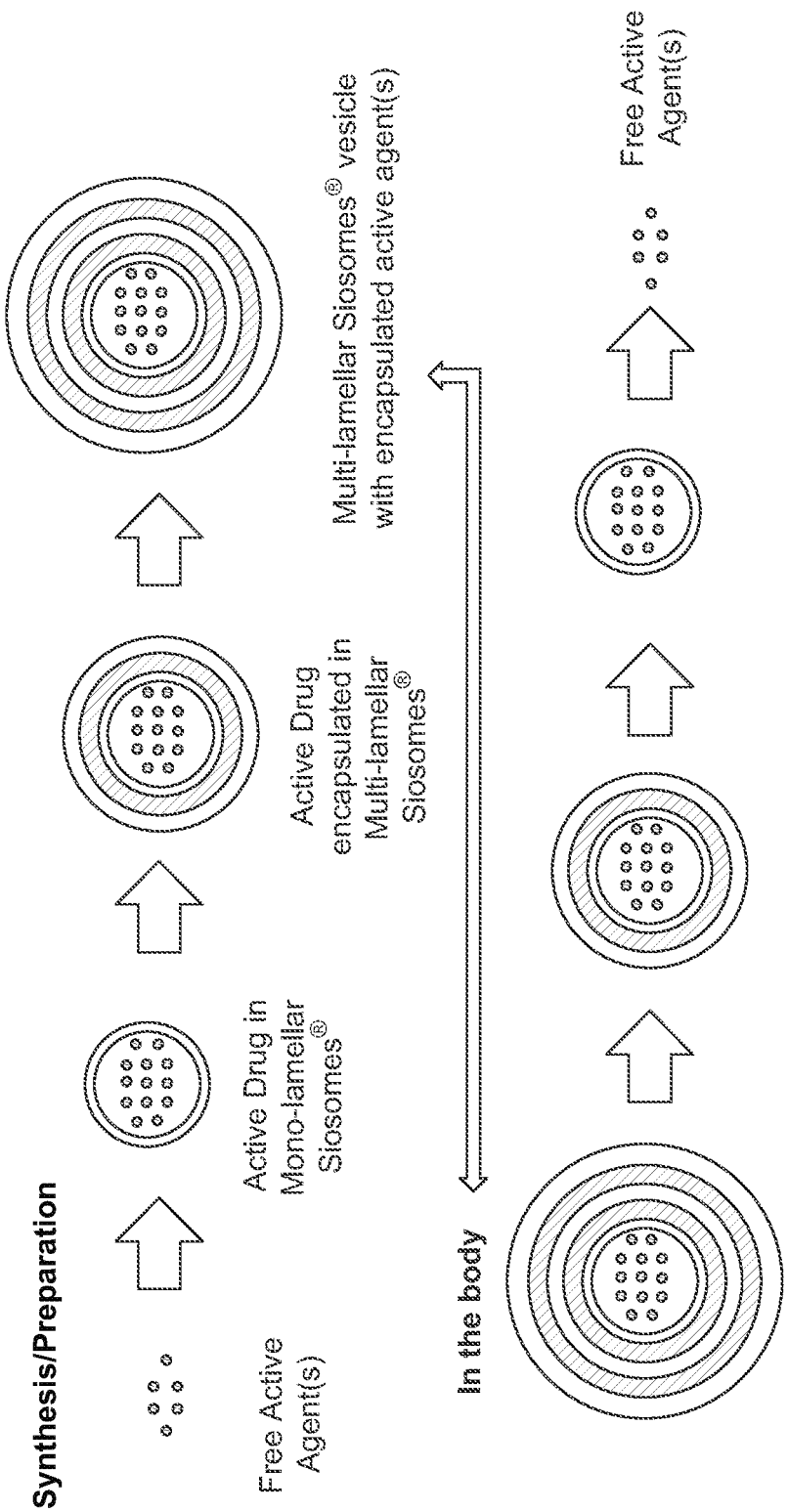
FIG. 7: Multi-target and delivery system using the Siosomes: Multi-Lameller siosomes vesicles with active drug.
Figure 8:
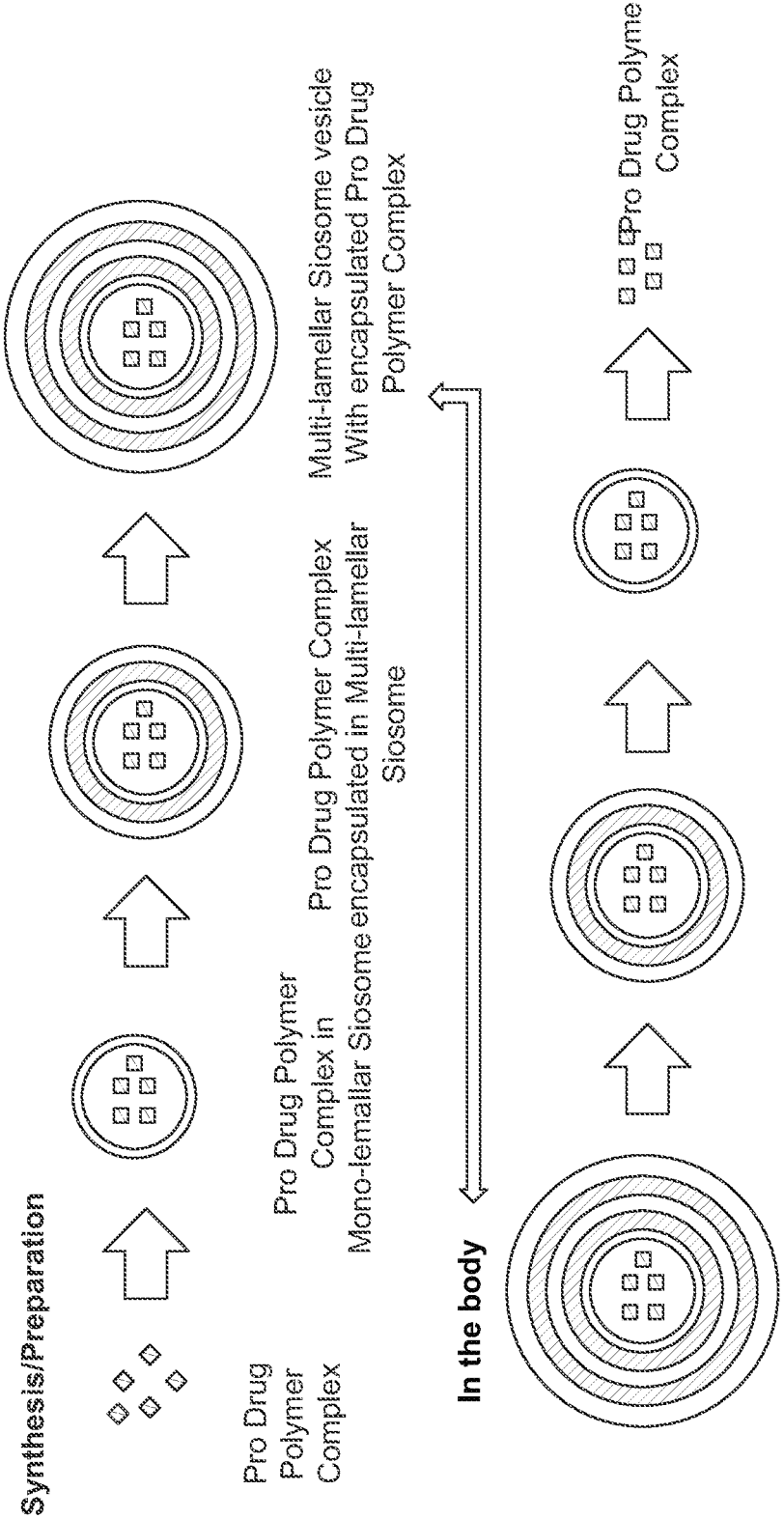
FIG. 8: Drug Delivery using Siosomes—Use of multilameller Siosomes vesicles as multi-target and delivery which reach the site of action with at least one intact vesicle layer and still contain the prodrug polymer complex.
Figure 9:
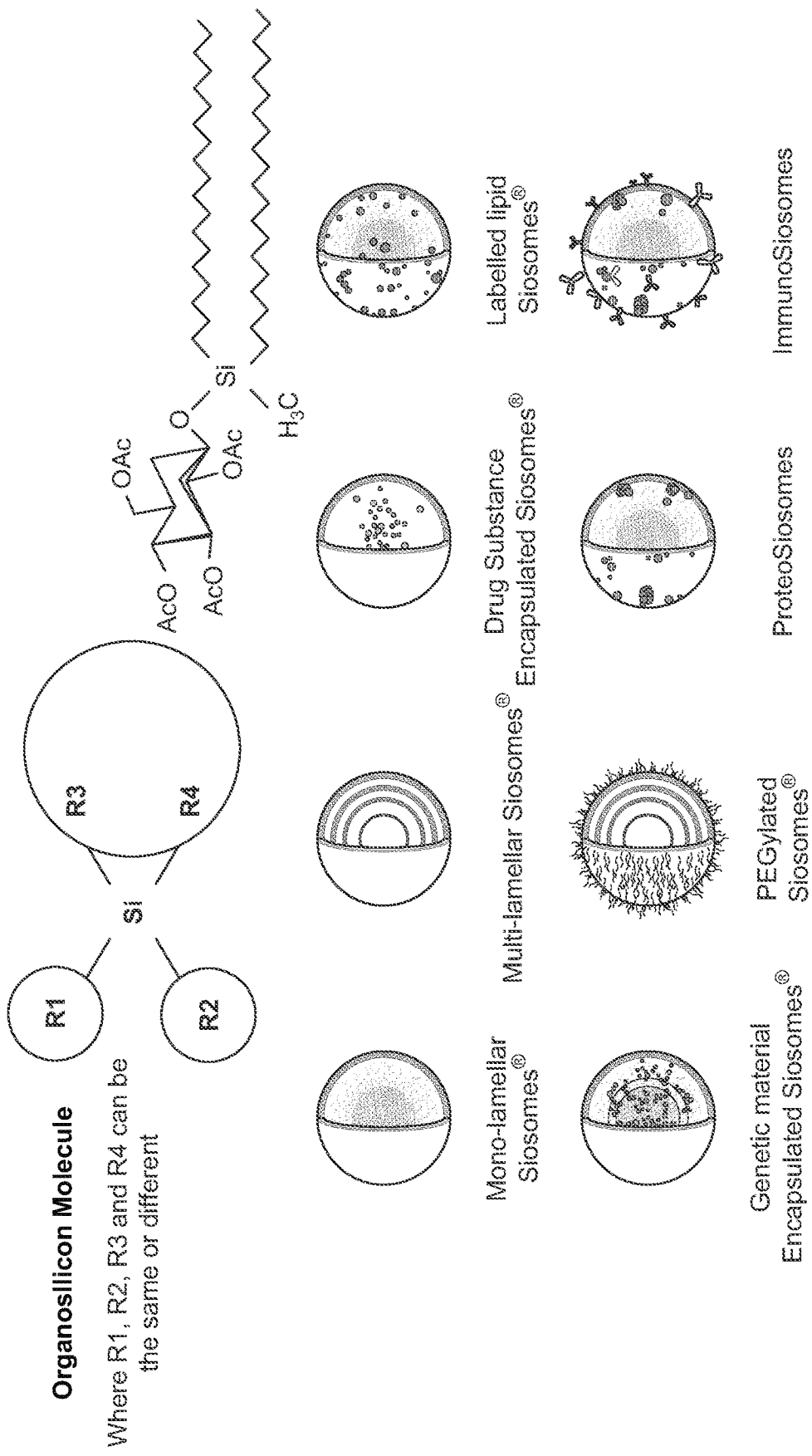
FIG. 9: Drug delivery and targeting system using the multi-target and delivery system the Siosomes-Flexibility of design for the delivery of lipid, genetic materials, proteoms, antigens and antibiotics.

The preparation of further siosomes from the modules 1, 2, 3 will be adjusted according to the customized molecular structure. And the residues R1, R2, R3, R4 and the molecules on the surface of the siosomes and/or encapsulated, entrapped and/or conjugated 2. Specific Multi-Targeting of the GI (Gastro Intestinal Tract)—(FIG. 6)

The oral route is attractive for drug administration because it is associated with patient acceptability, less stringent production conditions, and lower costs. Siosomes as multi-target and delivery system have many suitable properties for increasing the interaction between drugs and the mucosae. and targeting the receptors on the epithelial cells.

SARS Co-2 v and other viruses target and infect the GIT and the siosomes as the multi-target and delivery system will be able to block the ACE2 receptors in the host cells. In addition the inhibition of the virus via the blocking and inhibition of the spike protein (s) and the virion as explained in the functions of the siosomes of module 1, 2 and 3 according to the invention.

Furthermore, according to the invention the multi-target and delivery system could be administered orally, which will be as well of great advantage for the prophylaxis, attenuation, prevention and/or treatment of the infections caused by SARS Co-2 V.

The following specific GI compounds will be directly linked, encapsulated or entrapped in the siosomes:
N-Acetyl Cysteine
Glutamine
Fumarate
Glycolic Acid
Sodium Glycocholate
Sodium deoxy cholate
Sodium caprate
Lectins
Chitosan
Poly lactic 3. Specific Targeting the Brain-BBB Using the Siosomes as Multi-Target and Delivery System and CNS Navigators SARS Co-2 v and other viruses target and infect the CNS. Therefore it is an object of the invention to target the CNS.

Development of therapeutics for brain disorders is one of the more difficult challenges to be overcome by the scientific community due to the inability of most molecules to cross the blood-brain barrier (BBB). Antibody-conjugated nanoparticles are drug carriers that can be used to target encapsulated drugs to the brain endothelial cells and have proven to be very promising. They significantly improve the accumulation of the drug in pathological sites and decrease the undesirable side effect of drugs in healthy tissues. But they have serious problems concerning the very comprehensive development and production and stability of the monoclonal antibody complex.

The siosomes as multi-target and delivery system are pharmaceutical carriers and can provide very specific and stable targeting systems. A number of very specific navigators could be incorporated on the surface of the siosomes and be a part of the therapy strategy of the SARS Co-2 V.

The following neurotransmitters and compounds could be incorporated in the siosomes and as well encapsulated and/or entrapped in the siosomes:

Major neurotransmitters are listed below:

Amino acids: glutamate, aspartate, D-serine, γ-aminobutyric acid (GABA), glycine Gasotransmitters: nitric oxide (NO), carbon monoxide (CO), hydrogen sulfide ($H_2S$)

Monoamines: dopamine (DA), norepinephrine (noradrenaline; NE, NA), epinephrine (adrenaline), histamine, serotonin (SER, 5-HT)

Trace amines: phenethylamine, N-methylphenethylamine, tyramine, 3-iodothyronamine, octopamine, tryptamine, etc.

Peptides: oxytocin, somatostatin, substance P, cocaine and amphetamine regulated transcript, opioid peptides Purines: adenosine triphosphate (ATP), adenosine Catecholamines: dopamine, norepinephrine (noradrenaline), epinephrine (adrenaline)

Others: acetylcholine (ACh), anandamide, etc

The preparation of the multi-target and delivery systems will be performed according to the procedures of this invention.

Example 6

Figure 14:
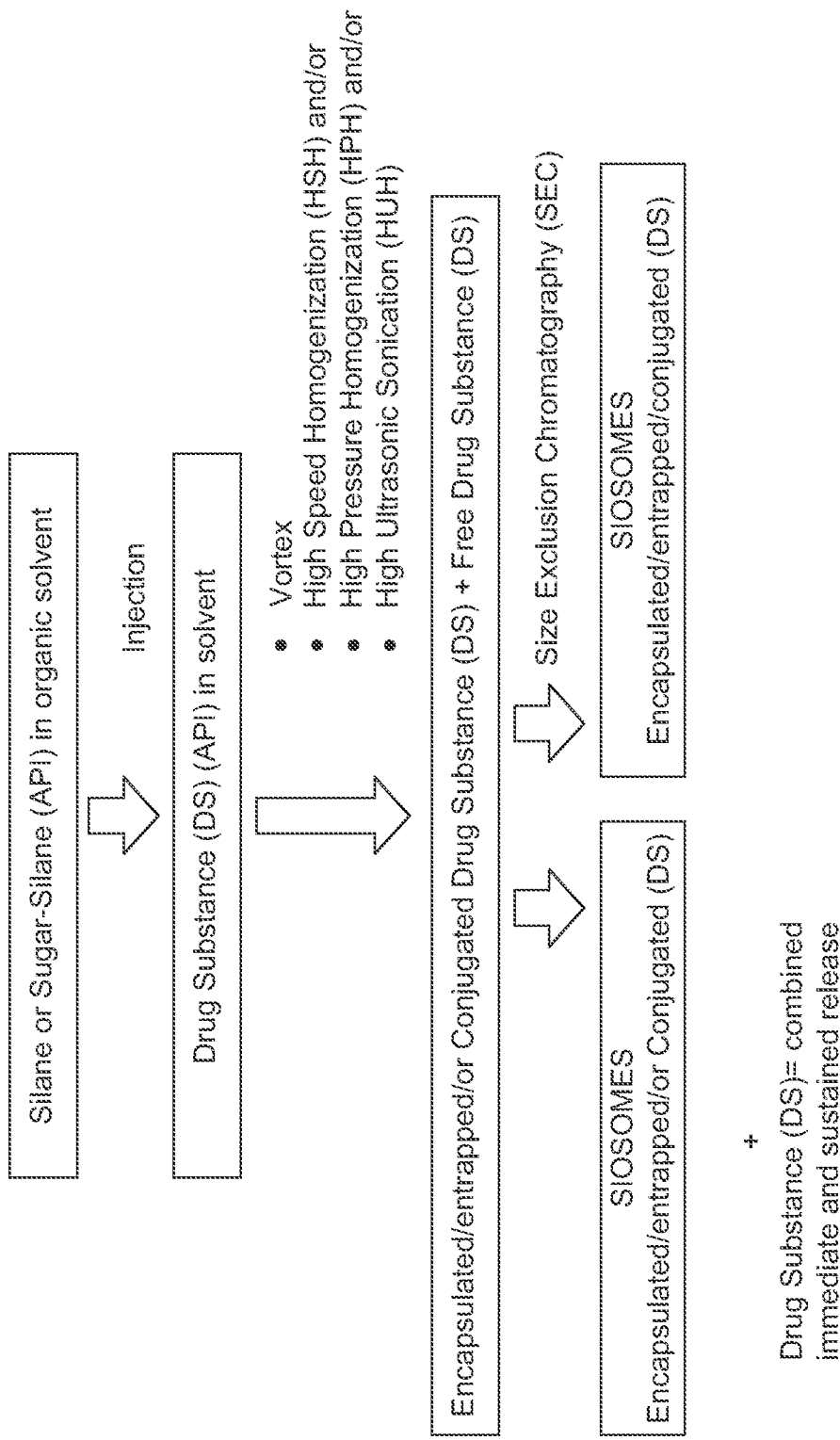
FIG. 14: Flowchart for the preparation of the Multi-Target and delivery siosomes system.

Preparation of the multi-target and delivery siosomes for the attenuation, prevention and/or treatment of the infections caused by the SARS Co 2-V Virur (FIGS. 14,15).

Examples for the structures of the sugar silanes and the siosomes from the Modules 1, 2, 3.1 and 3.2 are:

1. As an Example Silane/Siosome No. 2 Module 1 with Encapsulated Captopril (Table 1)

$$\text{Sugar} \diagdown \text{Si} \diagup \text{Lipid}$$
$$\text{Sugar} \diagup \quad \diagdown \text{Lipid}$$

2. As an Example Silane/Siosome No. 5 Module 2 with Encapsulated Dipeptide (Table 2)

$$\text{Sugar} \diagdown \text{Si} \diagup \text{Peptide}$$
$$\text{Sugar} \diagup \quad \diagdown \text{Lipid}$$

3. As an Example Silane/Siosome No. 3 Module 3.1 with Encapsulated m RNA (Table 3.1)

$$\text{Sugar} \diagdown \text{Si} \diagup \text{Lipid}$$
$$\text{Sugar} \diagup \quad \diagdown \text{Lipid}$$
$$\qquad \quad | $$
$$\qquad \text{PEG}$$

4. As an Example Silane/Siosome No. 1 Module 3.2 with Encapsulated Camostat Mesylate with Cationic Siosomes. Cam=Camostat—(Table 3.2)

$$\text{Sugar} \diagdown \text{Si} \diagup \text{Lipid}$$
$$\text{Sugar} \diagup \quad \diagdown \text{Lipid}$$
$$\qquad \quad | $$
$$\qquad \text{Cam----}$$

1. Preparation of any of the multi-targeting and delivery system (siosome) according to any one of the preceding claims, characterized in that the multi-targeting and delivery system is obtainable by:
   a) mixing one or more organosilicon, sugar organosilicon, amino-sugar organosilicon and/or the vesicles formed from them, with one or more of the active substances at selected pH, salt concentration and temperature;
   b) homogenisation, sonication and/or extrusion of the mixture, followed by c) separation of the free active substance,
   d) sterile filtration of the mixture,
   e) lyophilisation,
   f) reconstitution to form a siosome of the multi-target and delivery system.

2. The selected (customized) siosomes from module 1, 2, 3 with the defined functions will be prepared above according to the invention separately as lyophilized powder.

3. The lyophilized powder composition comprising siosomes 1, 2, 3 will be mixed at a ratio of X:Y:Z.

4. The mixed lyophilized powder will be used for the preparation of the following formulations: Oral, rectal, vaginal, topical, nasal, intradermal, or parenteral administration (FIG. 15).

The invention claimed is:

1. A method for treating, attenuating or inhibiting an infection and/or disease associated with a SARS CoV-2 virus in a subject, comprising administering a pharmaceutical composition to the subject, wherein the composition comprises three functional modules, each comprising an organosilicon carrier in the form of siosome nanoparticles, said modules comprising:
   Module 1: Siosomes with an ACE2 receptor inhibitor on the surface of the siosomes and/or an ACE2 inhibitor encapsulated, entrapped and/or conjugated in the siosomes, wherein said siosomes comprise at least one organosilicon compound covalently bound to a monosaccharide;
   Module 2: Siosomes with an inhibitor of the SARS virus spike protein on the surface of the siosomes and/or an inhibitor of the SARS virus spike protein encapsulated, entrapped and/or conjugated in the siosomes, wherein said siosomes comprise at least one organosilicon compound covalently bound to a monosaccharide; and
   Module 3: Siosomes with a polymerase inhibitor on the surface of the siosomes and/or a polymerase inhibitor encapsulated, entrapped and/or conjugated in the siosomes, wherein said siosomes comprise at least one organosilicon compound covalently bound to a cationic lipid and retaining a positive charge.

2. The method of claim 1, wherein the organosilicon carrier comprises at least one of sugar organosilicon or amino-sugar organosilicon compound according to the general formula (I):

$$R_1 \diagdown \quad \diagup R_3$$
$$\quad \text{Si}$$
$$R_2 \diagup \quad \diagdown R_4$$

whereby $R_1$, $R_2$, and $R_3$ can be the same or different;
whereby $R_1$, $R_2$, and $R_3$ are selected from the group consisting of a monosaccharide, a disaccharide, an oligosaccharide, an amino sugar, a carbohydrate, and a nucleotide, wherein at least one of $R_1$, $R_2$, $R_3$ is a monosaccharide; and
whereby R4 is a fatty acid.

3. The method of claim 1, wherein the organosilicon carrier is in the form of a siosome that is capable of penetrating the SARS-CoV-2 virus and inhibiting its function.

4. The method of claim 1, further comprising one or more active substances, selected from the group consisting of monoclonal antibodies, carbohydrate, lipids, amino acids, peptides, proteins, nucleosides, inhibitors of the lung cell receptors, antiviral agents, antibacterial agents, genetic materials, antigens, antibodies, immuno-agents, anti-inflammatory agents, antitumor agents, cardio-protectors, hepatoprotectors, GSH, oxidants, metal oxides, organosilicon compounds, Remdesivir, and corticosteroids, and wherein the one or more active substances are encapsulated, entrapped or conjugated in siosome nanoparticles.

5. The method according to claim 1, wherein the organosilicon carrier is obtained by:
   a) mixing at least one of organosilicon, sugar organosilicon, and amino-sugar organosilicon compounds in at least one of a solvent or vesicles, with the ACE2 receptor inhibitor, the inhibitor of SARS virus spike protein, and the polymerase inhibitor;
   b) homogenization, sonication and/or extrusion of the mixture, followed by
   c) separation of the free ACE2 receptor inhibitor, the inhibitor of SARS virus spike protein, and polymerase inhibitor
   d) sterile filtration of the mixture,
   e) lyophilization, and
   f) reconstitution to form a siosome of the multi-target and delivery system.

6. The method of claim 1, wherein the composition is a single or multiple dose formulation.

7. The method of claim 1, wherein the composition is administered via oral, rectal, vaginal, topical, nasal, intradermal, or parenteral administration, or as a transbuccal, sublingual, transmucosal or a sustained release formulation, wherein the parenteral administration is selected from the group consisting of subcutaneous, intravenous, intramuscular and infusion.

8. The method of claim 1, wherein the composition is administered in combination with additional antiviral therapies in patients with symptoms of a SARS-CoV-2 infection.

9. The method of claim 1, wherein the treatment comprises administration of a pharmaceutically effective dose of a second agent, selected from the group consisting of amino acids, carnitine/carnitine derivatives, neurotransmitters, vitamins, caffeine, antifibrotic agents, memory activating agents, neuroprotective agents, cardio-protective agents, antidiabetic agents, drugs for the prophylaxis and/or treatment of thrombosis, glutamate-antagonist, glutathione GSH, anti-Alzheimer's disease agents, antioxidants, anti-AIDS drugs, NSAIDS, antipsychotic drugs, buspirone, antidepressants, mood stabilizers, anticonvulsant, antigens, antibodies, genetic materials, catecholamines, hormones and sympatholytic adrenergic blocking agents.

10. The method of claim 1, wherein the at least one organosilicon compound covalently bound to a monosaccharide is at least one of
   2-(Dim ethyldecylsilylethyl-b-D-glucopyranoside,
   2-(Dimethyldodecylsilyl)ethyl-b-D-glucopyranoside,
   Butyldimethylsilyl-a-D-galactopyranoside,
   Dodecyldimethylsilyl-a-D-glucopyranoside,
   1-O-Dioctadecylsilyl-di(2,3,4,6-O-tetraacetyl-b-D-galactopyranoside),
   1-O-Dimethyl(dodecyl])silyl-)2,3,4,6-O-tetraacetyl-b-D-glucopyranoside),
   1-O-Dim ethyl(octadecyl)silyl-(2,3,4,6-O-tetraacetyl-b-D-glucopyranoside),
   Di(dodecanoyloxy)diphenylsilane,
   Dithexadecanoyloxy)diphenylsilane, or
   Di(undecanoyloxy)dimethylsilane.

11. The method of claim 1, wherein the organosilicon carrier further comprises neurotransmitters and/or amino acids as navigators incorporated on the surface of the siosomes, and/or conjugated to the siosomes, wherein said navigators are for the targeting of the brain and/or central nervous system.

12. The method of claim 1, wherein the organosilicon carrier further comprises gastro intestinal tract specific compounds, selected from the group consisting of N-acetyl cysteine, glutamine, fumarate, glycolic Acid, sodium glycol cholate, sodium deoxy cholate, sodium caproate, lectins, chitosan and Poly lactic acid, as navigators incorporated on the surface of the siosomes, and/or encapsulated, entrapped and/or conjugated in the siosomes, for the targeting of the gastro intestinal tract and/or colon.

* * * * *